US008419623B2

(12) United States Patent
Garcia et al.

(10) Patent No.: US 8,419,623 B2
(45) Date of Patent: Apr. 16, 2013

(54) PORTABLE ENDOSCOPE FOR DIVERSE MEDICAL DISCIPLINES

(75) Inventors: Alexander M Garcia, Street, MD (US); Karl Dallas Kirk, III, New York City, NY (US); Paul J Mulhauser, New York City, NY (US); Lyndon Thomas Treacy, Long Island City, NY (US)

(73) Assignee: CANI Optical Systems, LLC, Colora, MD (US)

( * ) Notice: Subject to any disclaimer, the term of this patent is extended or adjusted under 35 U.S.C. 154(b) by 1048 days.

(21) Appl. No.: 12/361,533

(22) Filed: Jan. 28, 2009

(65) Prior Publication Data

US 2010/0191053 A1 Jul. 29, 2010

(51) Int. Cl.
*A61B 1/00* (2006.01)

(52) U.S. Cl.
USPC ............................................ 600/136; 600/149

(58) Field of Classification Search ............. 600/18–149
See application file for complete search history.

(56) References Cited

U.S. PATENT DOCUMENTS

| 4,911,148 | A | 3/1990 | Sosnowski et al. |
| 5,411,020 | A | 5/1995 | Ito |
| 5,489,256 | A | 2/1996 | Adair |
| 6,494,827 | B1 | 12/2002 | Matsumoto et al. |
| 7,828,723 | B2 * | 11/2010 | Ueno et al. .................... 600/136 |
| 8,021,293 | B2 * | 9/2011 | Dejima et al. ................ 600/104 |
| 2006/0100640 | A1 * | 5/2006 | Bolduc ......................... 606/108 |
| 2007/0167679 | A1 * | 7/2007 | Miyamoto et al. ............ 600/106 |
| 2008/0051631 | A1 * | 2/2008 | Dejima et al. ................ 600/114 |
| 2008/0091064 | A1 | 4/2008 | Laser |
| 2008/0214896 | A1 * | 9/2008 | Krupa et al. .................. 600/136 |

FOREIGN PATENT DOCUMENTS

JP 07-178041 A 7/1995

* cited by examiner

*Primary Examiner* — Alireza Nia

(74) *Attorney, Agent, or Firm* — Ash Tankha; Lipton, Weinberger & Husick

(57) ABSTRACT

Disclosed herein is a portable endoscope and kit for performing multiple medical procedures. The portable endoscope comprises a detachable operator control section assembly and one of multiple detachable and interchangeable flexible insertion shaft assemblies with a flexible distal end. The proximal end of a detachable and interchangeable flexible insertion shaft assembly is detachably connected to the detachable operator control section assembly. The detachable and interchangeable flexible insertion shaft assembly accommodates principal cable wires, proxy cable wires, an optical imaging system, and an illumination system. An internal cable wire control system integrated with the detachable operator control section assembly utilizes an adaptable drive transmission system for controlling the orientation and angular position of the flexible distal end using the principal cable wires or the proxy cable wires. The proxy cable wires may be engaged in an event of failure of the principal cable wires.

3 Claims, 26 Drawing Sheets

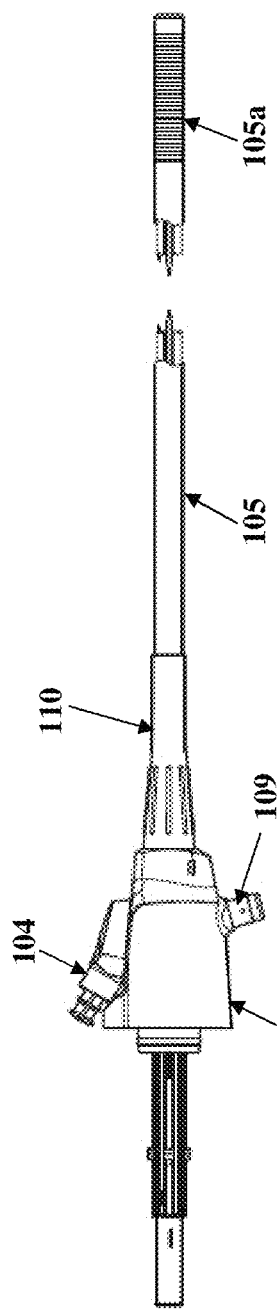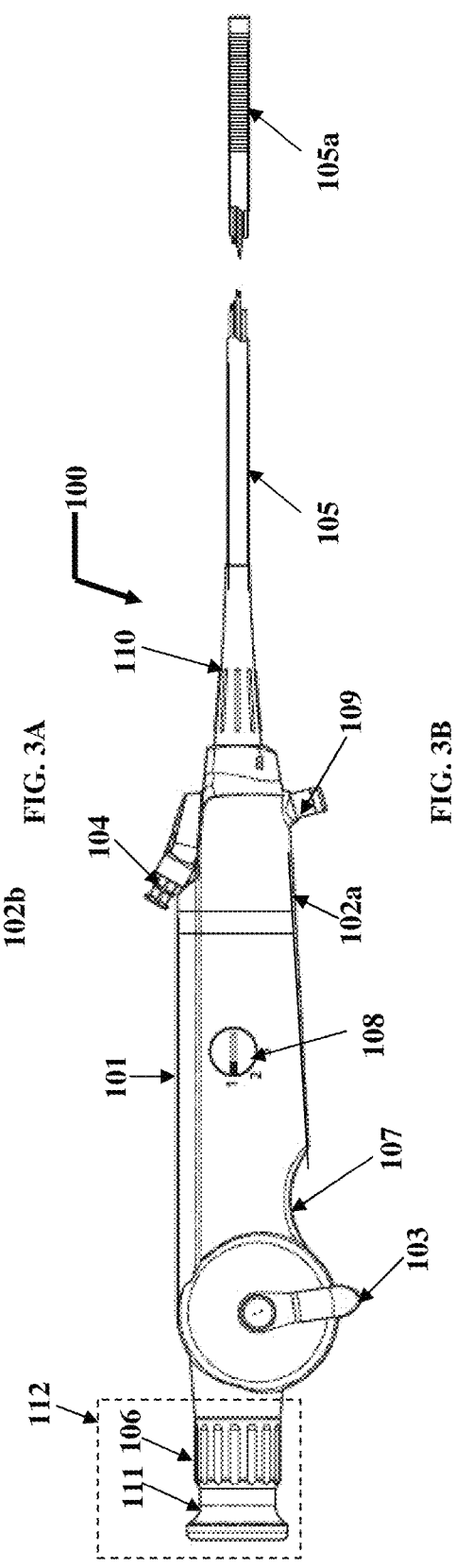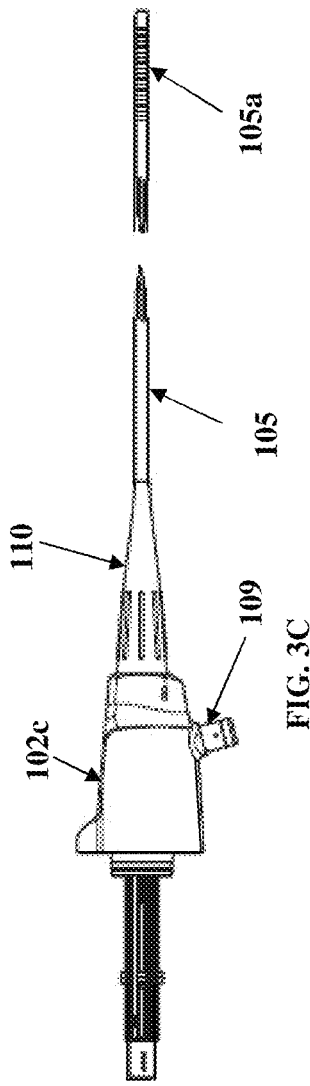

PORTABLE ENDOSCOPE FOR DIVERSE MEDICAL DISCIPLINES

BACKGROUND

This invention, in general, relates to an endoscope for viewing inaccessible cavity regions of a body. More particularly, this invention relates to a portable endoscope for diverse medical disciplines.

Typically, a medical specialty, for example, otolaryngology, urology, anesthesia, bronchoscopy, gastroenterology, hysteroscopy, etc. requires a unique endoscope to perform procedures in that medical specialty. This requires a medical establishment providing medical services to purchase, stock, and maintain endoscopes and parts of the endoscope for the medical specialties for which services are provided. Procurement and maintenance of such endoscopes increases the overhead cost of the medical establishment and the cost of such medical procedures. Partly because endoscope and endoscope parts used in different medical procedures are not interchangeable, dedicated endoscopes for each discipline are required to be inventoried. If different endoscopes are not maintained in an inventory at the medical establishment, obtaining them in a timely fashion for the performance of a procedure is also an issue.

Typically, endoscopes are characterized by different structural configurations that enable an operator of an endoscope to control angular movements of a flexible distal end of the endoscope. A typical endoscope comprises a single integrated functional unit with no detachable components. Endoscopes are generally structurally configured with external light cords or cables, connected to an external light source, a video processing source, or both. The cords and the cables may restrict the use of the endoscope at a desired location in the body, or limit the flexibility, movement, or maneuverability of the endoscopes for performing a medical procedure.

Typically, commercial endoscopes utilizing a portable battery pack, fiber optic cables, and cords have no or minimal detachable components. Over time and usage, components in the endoscopes, for example, the fiber optic cables, electrical components, components for controlling movements of the flexible distal end, etc. may wear, break, or experience a failure or become dysfunctional due to faulty use, or accidental breakage. When such a failure occurs, such endoscopes without detachable components may be difficult to repair and reuse and therefore require an entire replacement endoscope to be maintained in inventory.

When the components of an endoscope experience a failure during a medical procedure, the medical procedure generally requires the withdrawal of the endoscope inserted into the body of a patient. The medical practitioner may then need to procure a new endoscope and restart the medical procedure on the patient. The time delay involved in procuring the new endoscope and restarting the medical procedure may extend the time necessary to complete the medical procedure and cause medical complications and patient discomfort, for example, during reinsertion of the endoscope, etc. The time lag may also cause additional delays in prescheduled procedures. Also, in case of failure of an endoscope during a medical procedure, the endoscope may not be provided with a built-in or another alternative to continue or resume the procedure immediately. Hence the endoscopes may be inoperable in an event of failure during a medical procedure.

Conventional endoscopes of different sizes, lengths, and ranges of deflection or steering are used depending on the procedure to be performed, the orifice used to gain access, and the specific body cavity to be reached. Steering is achieved by pulling on one of multiple control lines that are embedded within the insertion shaft bundle. Pulling on the left control line causes the distal tip to deflect to the left, pulling on the right causes deflection to the right, on the top upward, and so forth. The amount of control line pull required to achieve a desired amount of distal tip deflection is directly proportional to the diameter of the insertion shaft bundle and the amount of deflection sought. In other words, the larger the endoscope, the greater pull required, plus the greater the deflection, the longer the required pull. For a typical endoscope, this pull requirement may, for example, deviate by $1/8$ inches from neutral or smaller for the smallest endoscopes with limited steering, for example, from 90 degrees, to a deviation of $5/8$ inches from neutral or larger, for example, 270 degrees for the largest endoscopes.

To steer an endoscope, a simple thumb lever is typically used to translate the sweep of the operator's thumb, moving from a neutral position to flexion and extension, into pull upon the appropriate control line. For an ordinary endoscope with a typical handgrip posture, this lever swing may be limited to 45 degrees to 50 degrees of thumb lever angulation. This coincides with the reach of an operator's thumb which is limited by length and the distance covered from full flexion to full extension.

In typical endoscopes where the flexible insertion shaft is integral and not detachable from the hand control, fixed internal gearing or levers may translate the thumb lever swing into a predetermined range of pull action that corresponds with the requirements and range of the integral flexible insertion shaft so that the entire swing of the thumb controls the entire range of steering.

Hence, there is a need for a portable endoscope comprising detachable components to eliminate dependency on external cords, cables, and related accessories required to perform the medical procedures. There is also a need for a portable endoscope with detachable components that is configurable for use in diverse medical specialties and disciplines and associated medical procedures. Furthermore, there is a need for an endoscope with internal back-up systems and redundancies to allow immediate remedy and recovery from component failures or break downs.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The portable endoscope disclosed herein comprises a detachable operator control section assembly, with an internal cable wire control system, and one of multiple detachable and interchangeable flexible insertion shaft assemblies. An operator may select one of the flexible insertion shaft assemblies based on the endoscopic task to be performed. For example, the operator may select a small-diameter flexible insertion shaft assembly to inspect a paranasal sinus of a patient. Alternatively, the operator may select a relatively large-diameter flexible insertion shaft assembly to inspect the patient's gastrointestinal tract. The operator may attach the selected flexible insertion shaft assembly to the operator control section assembly to form a complete portable endoscope ready to perform the needed endoscopic procedure.

The assembled portable endoscope comprises a pair of principal cable wires within the body of the flexible insertion shaft assembly. The principal cable wires are attached to opposing sides of the distal end of the flexible insertion shaft assembly and are selectably attached by an adaptable drive transmission system to a steering lever on the operator control section assembly. The operator manipulates the steering lever to pull on one of the principal cable wires and to push on the other of the principal cable wires, thus causing the distal end of the flexible insertion shaft assembly to deflect a controlled amount.

The amount of deflection is determined by the diameter of the flexible insertion shaft assembly and the amount of linear movement of the principal cable wires within the body of the flexible insertion shaft assembly. For example, a small-diameter flexible insertion shaft assembly will require less linear movement of the principal cable wires than a large-diameter flexible insertion shaft assembly for the same amount of deflection of the distal end of the flexible insertion shaft assembly.

The adaptable drive transmission system automatically selects the range of deflection of the distal end of the flexible insertion shaft assembly and automatically adapts to differences in diameter of the different flexible insertion shaft assemblies. The operator may select flexible insertion shaft assemblies so that a given deflection of the steering lever by the operator results in a similar deflection of the distal end of any flexible insertion shaft assembly, regardless of the diameter of the selected flexible insertion shaft assembly. In addition, the operator may select different ranges of deflection for flexible insertion shaft assemblies of the same diameter.

To accomplish the automatic selection of the range of deflection of the distal end of the flexible insertion shaft assembly, the steering lever is attached to a crank lever. The steering lever and the crank lever rotate about a common axis in response to movement of the steering lever by the operator. The crank lever moves a connecting rod to push and pull the principal cable wires. The effective length of the crank lever is changed automatically by a shifter plate that moves with the steering lever and the crank lever about the common axis of rotation. The shifter plate defines a spiral cam that defines the location of the connection between a crank arm and the crank lever and hence defines the effective length of the crank lever.

The rotational position of the shifter plate with respect to the crank lever, and hence the effective length of the crank lever, is defined by the selected flexible insertion shaft assembly. The selected flexible insertion shaft assembly defines a shifter rod on the proximal end of the flexible insertion shaft assembly. When the selected flexible insertion shaft assembly is attached to the operator control section assembly, the shifter rod bears upon a rack, which rotates a pinion attached to the shifter plate. Rotating the pinion causes the shifter plate, and hence the spiral cam, to turn with respect to the crank lever, thereby selecting the effective length of the crank lever. The length of the shifter rod of the selected insertion shaft assembly therefore determines the effective crank lever length and the amount of deflection of the distal end of the flexible insertion shaft assembly for a given movement of the steering lever by the operator.

The body of the flexible insertion shaft assembly accommodates the principal cable wires, proxy cable wires, an optical imaging system, and an illumination system. The flexible insertion shaft assembly may also incorporate a working channel. The proxy cable wires act as a backup for the principal cable wires and may be engaged in the event of failure of the principal cable wires.

The portable endoscope further comprises a cable wire switch integrated with the flexible insertion shaft assembly to engage the principal cable wires or the proxy cable wires with the adaptable drive transmission system. The internal cable wire control system comprises a steering lever for controlling angular movements of the flexible distal end of each of the flexible insertion shaft assemblies. The steering lever manipulates movement of the principal cable wires or the proxy cable wires engaged with the internal cable wire control system via the adaptable drive transmission system. The internal cable wire control system may utilize the proxy cable wires for operating the portable endoscope in the event of failure of the principal cable wires during one of the medical procedures in progress. In the event of failure of the principal cable wires, the cable wire switch disengages the principal cable wires from the adaptable drive transmission system and engages the proxy cable wires with the adaptable drive transmission system. The adaptable drive transmission system comprises an angulation and deflection gear system with gears and gear track subassemblies for matching operator input to steering output of the portable endoscope. The portable endoscope may further comprise a neutral lock-out system and a quick disconnect subassembly for facilitating engagement and disengagement of the principal cable wires and the proxy cable wires.

The portable endoscope further comprises an external light source in communication with the illumination system and the optical imaging system. The external light source provides light to the illumination system and the optical imaging system. The optical imaging system integrated with the portable endoscope captures and transmits visual images received from the flexible insertion shaft assembly. The optical imaging system may utilize the illumination system for illumination during the capture and transmission of the visual images. The visual images captured and transmitted by the optical imaging system may be displayed on a visual display unit provided on the operator control section assembly. Optionally, the visual images may also be displayed on an external visual display unit. The portable endoscope may further comprise a working channel turret integrated with the flexible insertion shaft assembly for aiding different medical procedures, for example, lavage, aspiration, biopsy, or manipulation. The portable endoscope may further comprise a suction and irrigation control system for controlling flow of fluids during a medical lavage or aspiration procedure. The suction and irrigation control system may be detachably attached to the detachable operator control section assembly.

The portable endoscope disclosed herein may be provided in a kit. The portable endoscope kit comprises component parts capable of being assembled in the field. The component parts are an operator control section assembly and multiple flexible insertion shaft assemblies. The flexible insertion shaft assemblies included in the kit may be used for different purposes. For example, a first flexible insertion shaft assembly selected from the flexible insertion shaft assemblies may be configured for an endoscopic purpose different from a second flexible insertion shaft assembly selected from the flexible insertion shaft assemblies. Each of the flexible insertion shaft assemblies comprises an elongated body with a distal end and a proximal end. Each of the distal ends and each of the elongated bodies are configured for insertion into an internal cavity of a body of a living organism. The proximal end of each of the flexible insertion shaft assemblies is configured for selectable engagement between the proximal end and the operator control section assembly.

The operator control section assembly is configured to engage the proximal end of any one of the flexible insertion shaft assemblies. The distal end of each of the flexible insertion shaft assemblies is locally bendable. Each of the flexible insertion shaft assemblies and the operator control section assembly are configured so that the operator control section assembly selectably controls the local bending of the distal end of the flexible insertion shaft assembly when the flexible shaft assembly is in the selectable engagement with the operator control section assembly.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

FIGS. 3A-3C exemplarily illustrate different detachable and interchangeable flexible insertion shaft assemblies that may be used in conjunction with a detachable operator control section assembly of a portable endoscope based on predefined functional requirements of the portable endoscope specified for each of the medical disciplines and associated medical procedures.

DETAILED DESCRIPTION OF THE INVENTION

Figure 1:
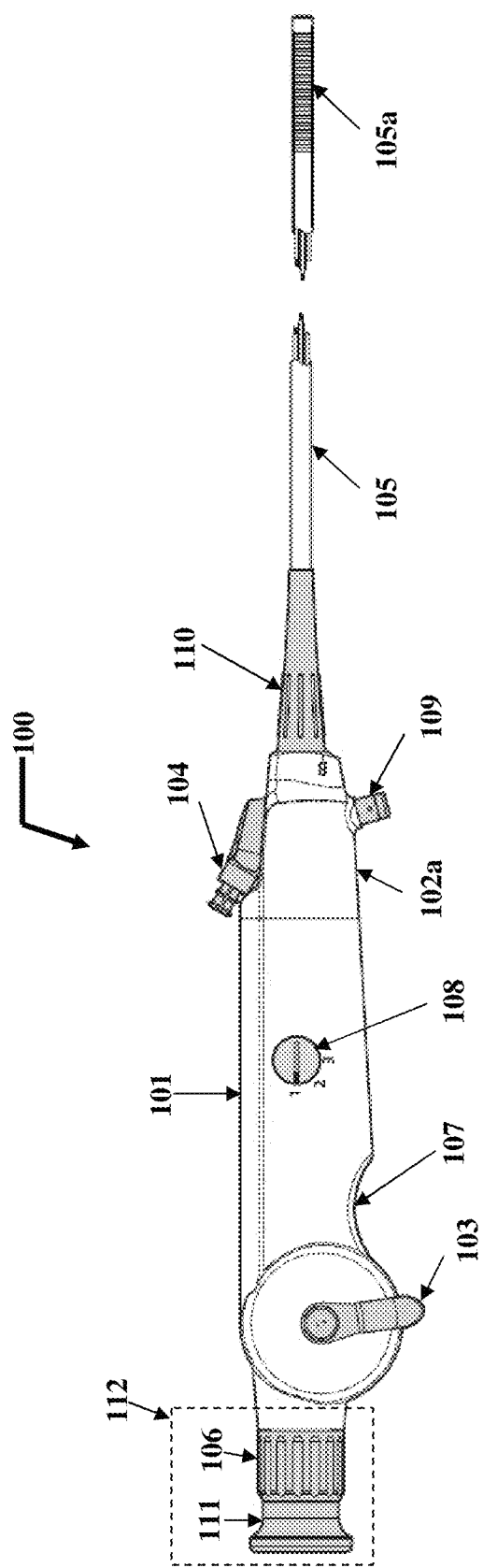
FIG. 1 exemplarily illustrates a portable endoscope for diverse medical disciplines and associated medical procedures.

FIG. 1 exemplarily illustrates a portable endoscope 100 for diverse medical disciplines and associated medical procedures. The portable endoscope 100 disclosed herein comprises a detachable operator control section assembly 101, and a detachable and interchangeable shaft assembly 102a with a flexible distal end 105a. The detachable operator control section assembly 101 may be provided with a hand grip rim 107 to facilitate a stable and secure hand grip on the portable endoscope 100 during the medical procedures. The hand grip rim 107 is a configured surface provided on the body of the detachable operator control section assembly 101 for the hand grip. The detachable and interchangeable shaft assembly 102a and the detachable and interchangeable flexible insertion shaft assemblies 102a, 102b, and 102c are herein referred to as a "shaft assembly" and "shaft assemblies" respectively. An operator may select a shaft assembly 102a from the shaft assemblies 102a, 102b, and 102c for a particular medical discipline procedure based on the endoscopic procedure to be performed. For example, the operator may select a small-diameter shaft assembly to inspect a paranasal sinus of a patient. Alternatively, the operator may select a relatively large-diameter shaft assembly to inspect the patient's gastrointestinal tract.

Figure 4A:
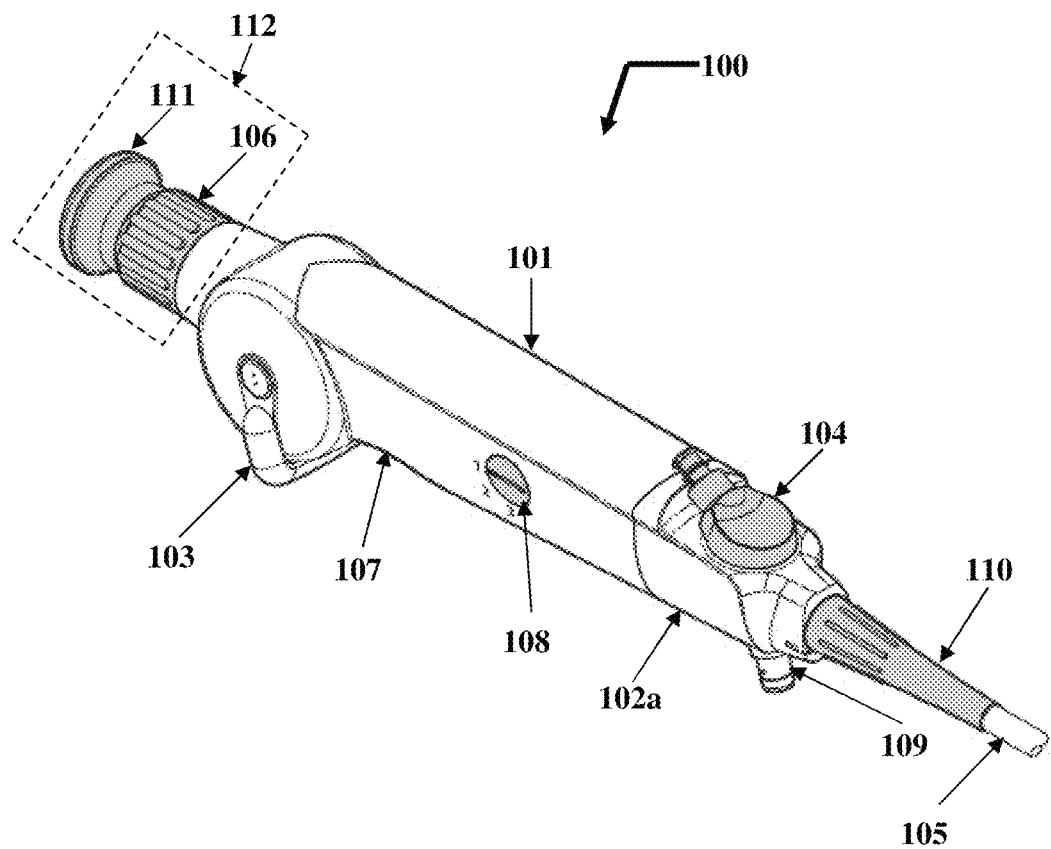
FIG. 4A exemplarily illustrates an isometric top view of a portable endoscope for diverse medical disciplines and associated medical procedures.
Figure 4B:
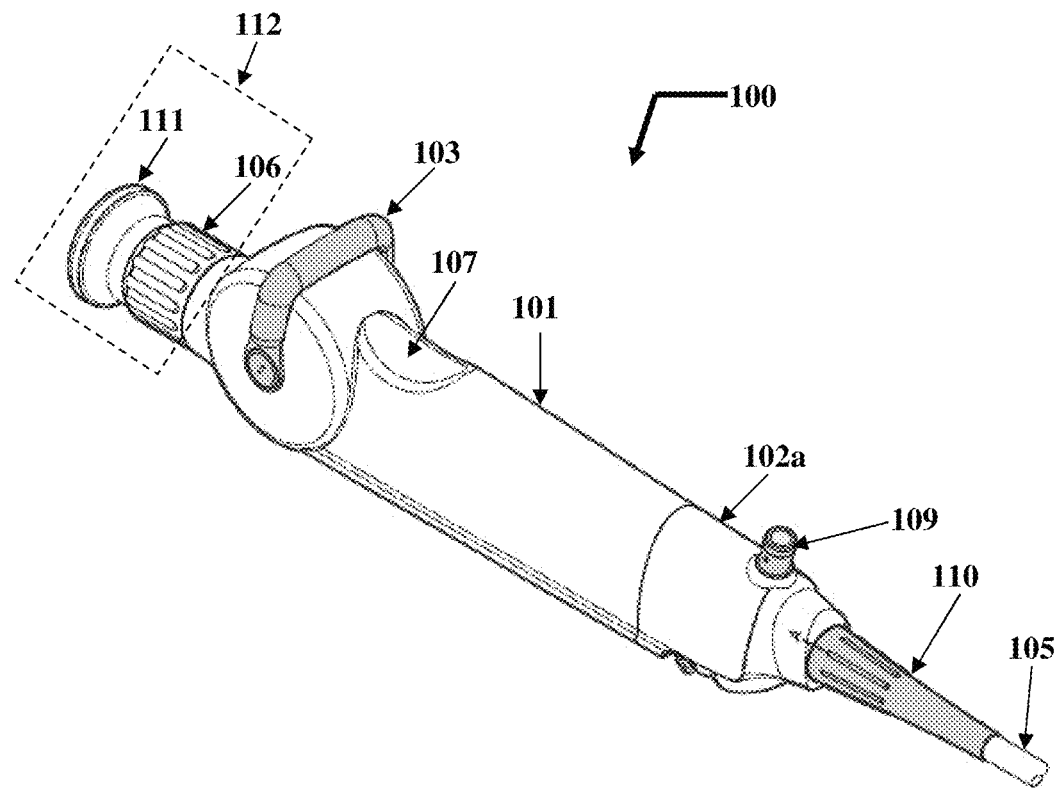
FIG. 4B exemplarily illustrates an isometric bottom view of a portable endoscope for diverse medical disciplines and associated medical procedures.
Figure 4C:
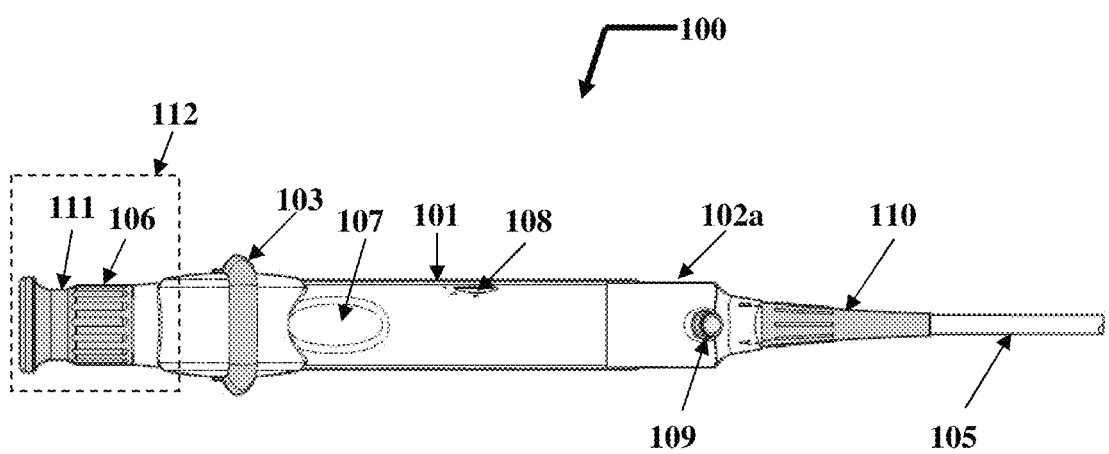
FIG. 4C exemplarily illustrates an orthographic bottom view of a portable endoscope for diverse medical disciplines and associated medical procedures.

The proximal end of the selected shaft assembly 102a is detachably connected to the detachable operator control section assembly 101. The operator may attach the selected shaft assembly 102a to the detachable operator control section assembly 101 to form a complete portable endoscope 100 ready to perform the needed endoscopic procedure. The detachable operator control section assembly 101 and a shaft assembly 102a are exemplarily illustrated in FIG. 2. Different shaft assemblies, for example, shaft assemblies 102a, 102b, and 102c may be interchangeably used in conjunction with the detachable operator control section assembly 101 of the portable endoscope 100 based on predefined functional requirements, the end use or application of the portable endoscope 100 as illustrated in FIGS. 3A-3C. The medical disciplines may, for example, be otolaryngology, urology, intubations, anesthesia, bronchoscopy, gastroenterology, gynecology, hysteroscopy, etc. An isometric top view of the portable endoscope 100 for diverse medical disciplines and associated medical procedures is exemplarily illustrated in FIG. 4A. An isometric bottom view of the portable endoscope 100 for diverse medical disciplines and associated medical procedures is exemplarily illustrated in FIG. 4B. An orthographic bottom view of the portable endoscope 100 for diverse medical disciplines and associated medical procedures is exemplarily illustrated in FIG. 4C. For a particular medical procedure or medical discipline, one of the shaft assemblies 102a, 102b, and 102c is attached to the detachable operator control section assembly 101.

Figure 2:
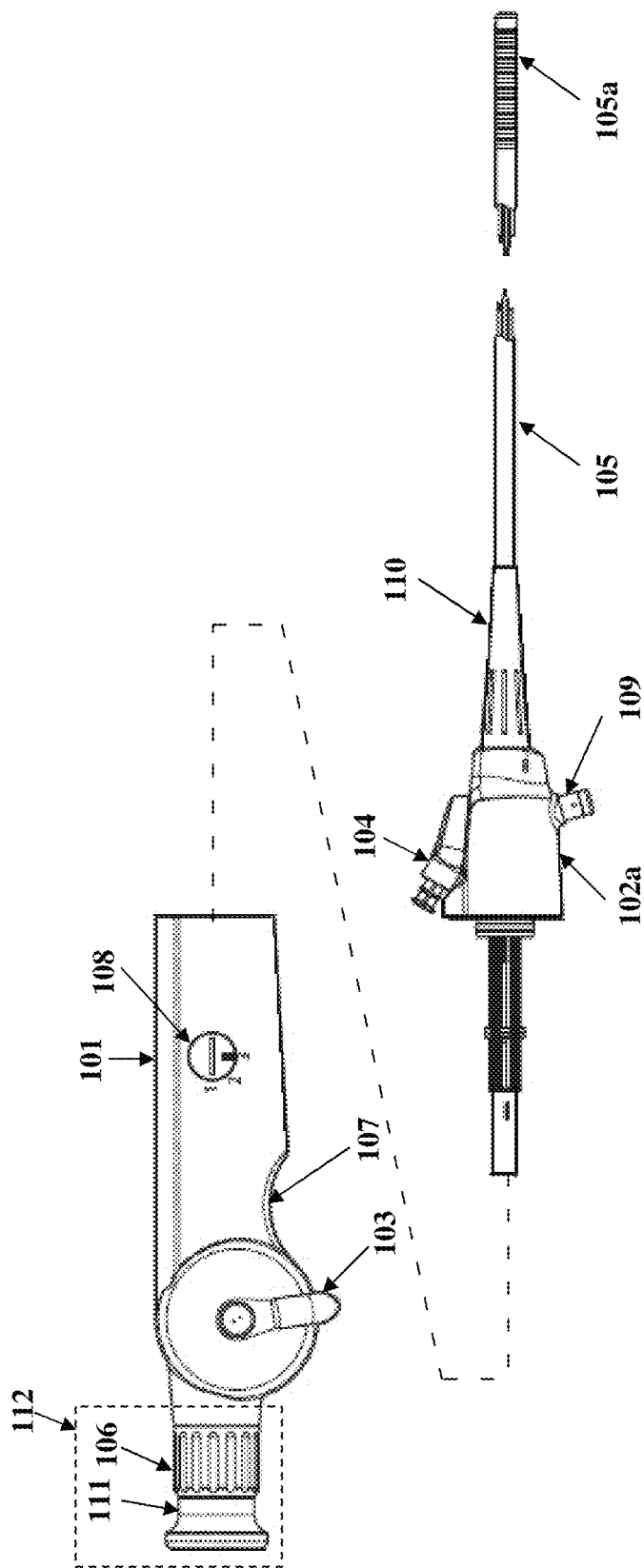
FIG. 2 exemplarily illustrates a detachable operator control section assembly and a detachable and interchangeable flexible insertion shaft assembly of a portable endoscope for diverse medical disciplines and associated medical procedures.
Figure 5A:
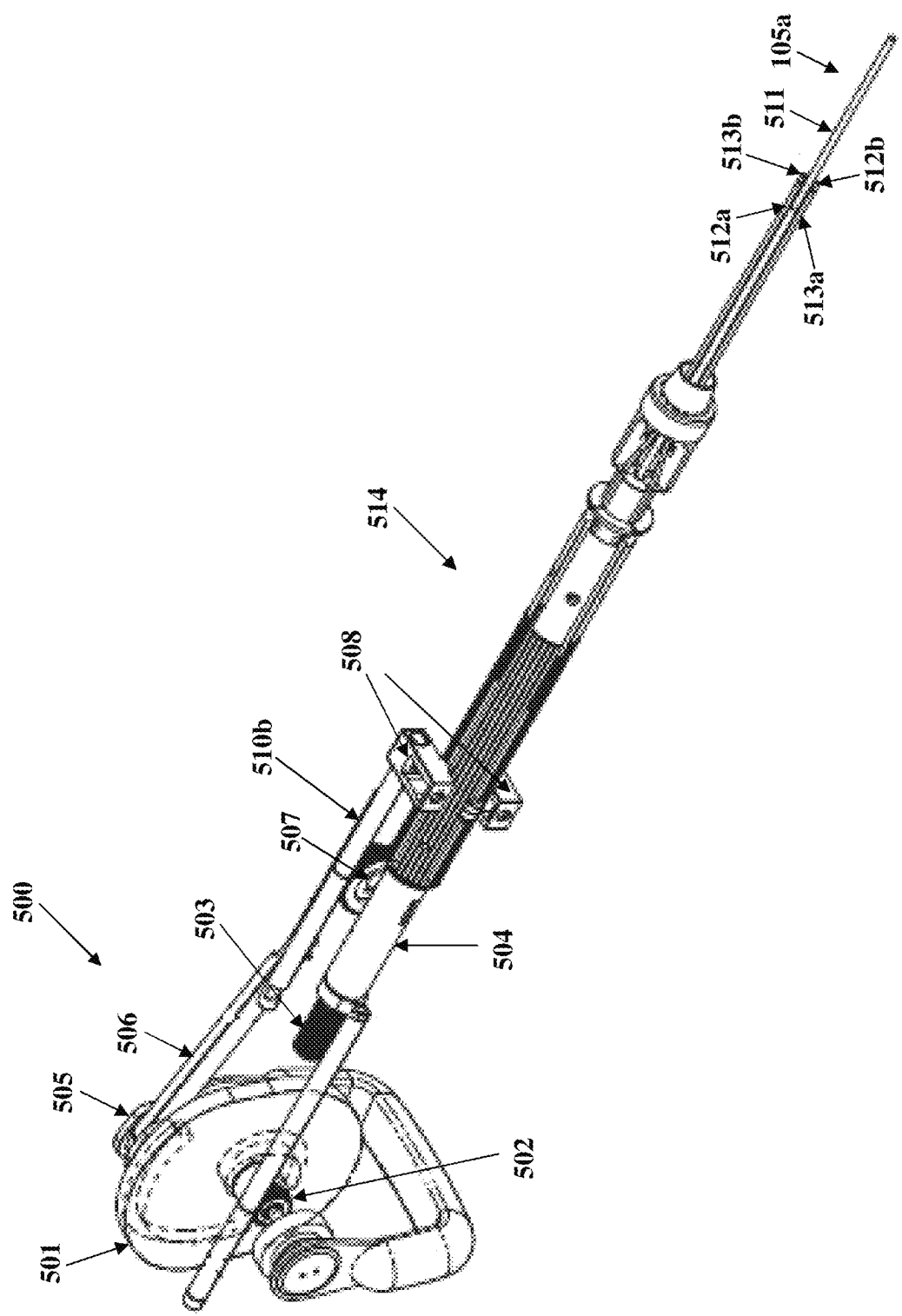
FIGS. 5A-5B exemplarily illustrate an internal cable wire control system and an adaptable drive transmission system of a portable endoscope for diverse medical disciplines and associated medical procedures.
Figure 5B:
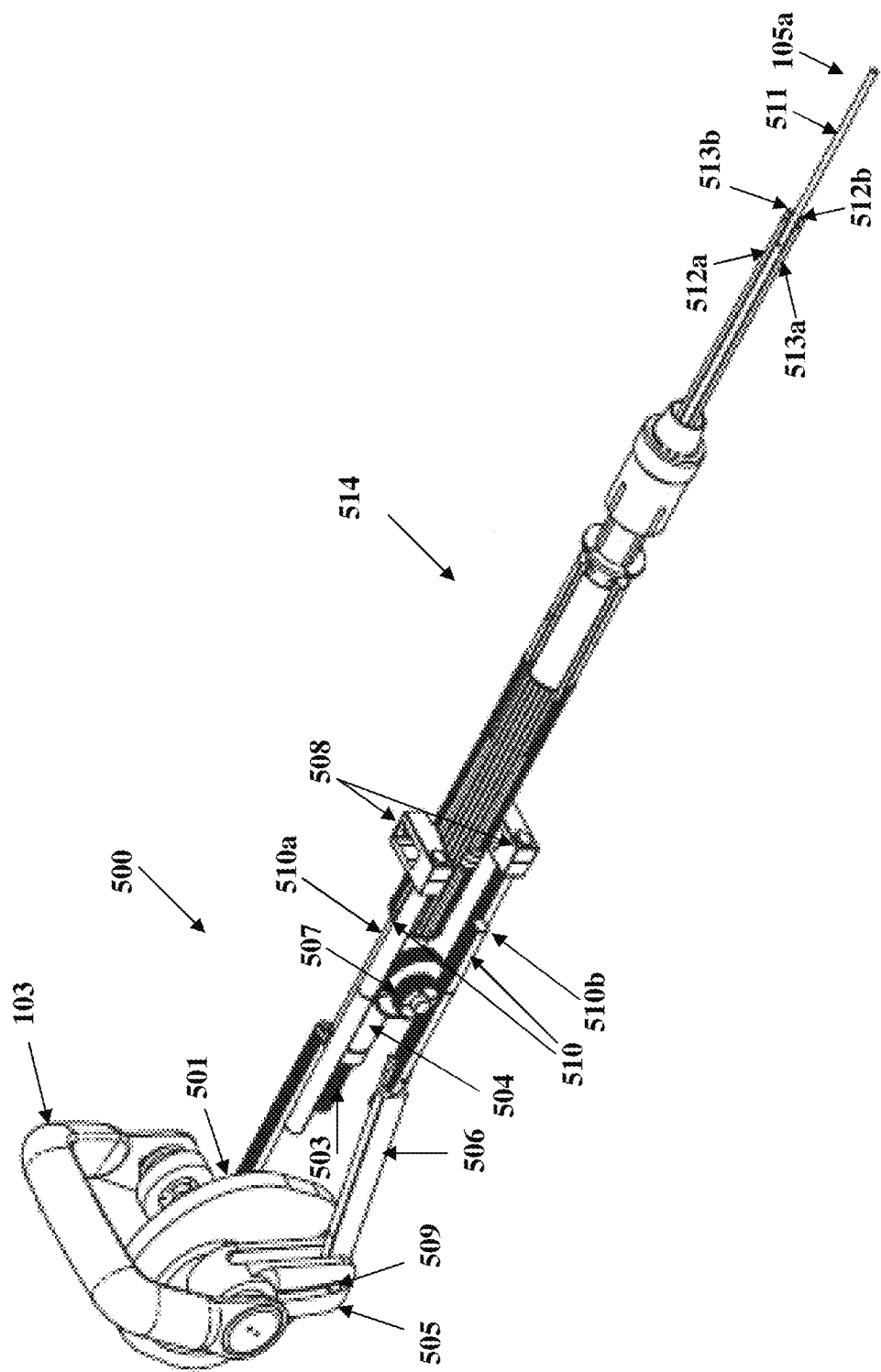
Figure 11:
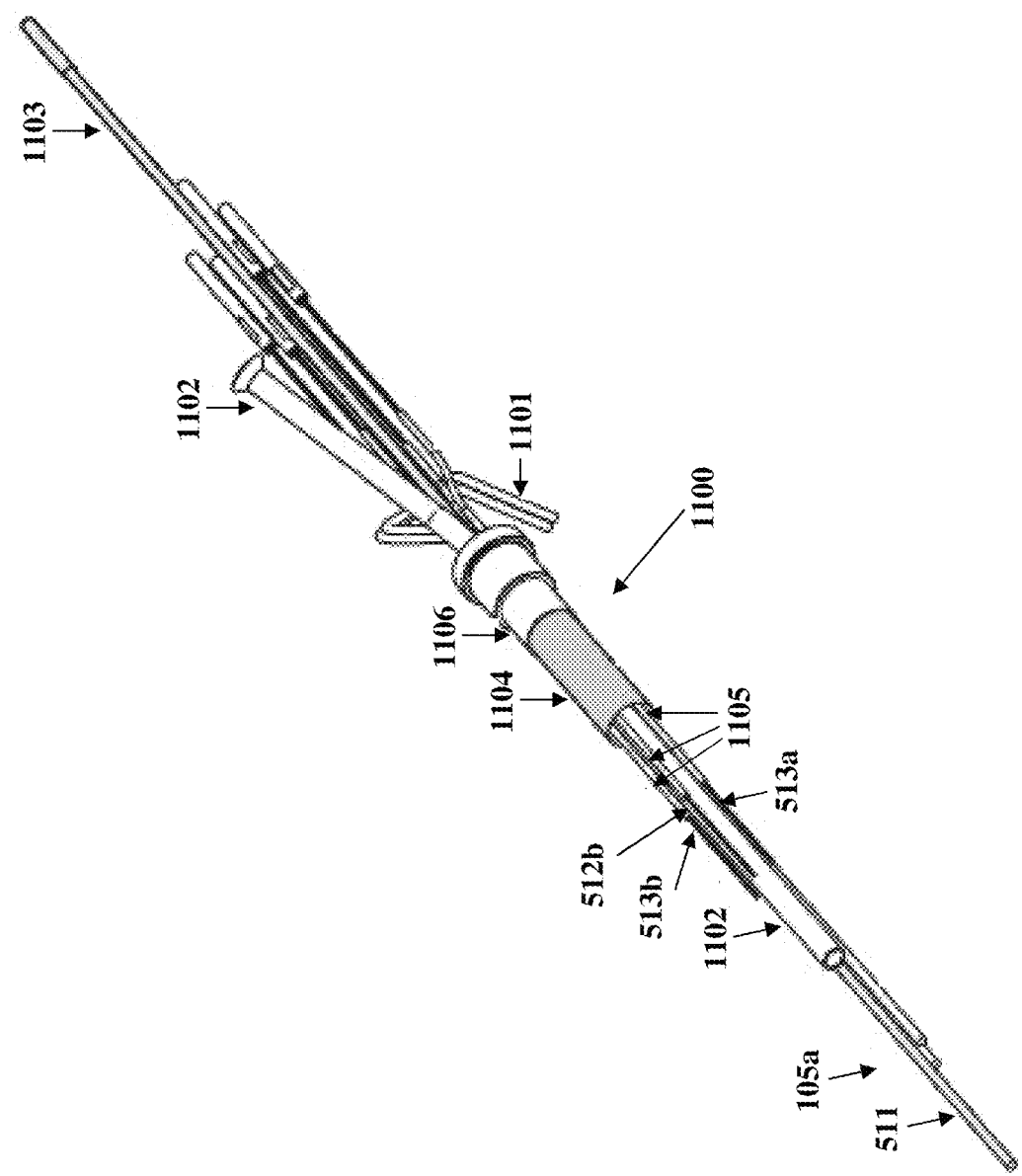
FIG. 11 exemplarily illustrates internal components of the flexible insertion shaft bundle of the detachable and interchangeable flexible insertion shaft assembly.

The shaft assembly 102a accommodates principal cable wires 512a and 512b, proxy cable wires 513a and 513b, an optical imaging system 112, and an illumination system 1101. The principal cable wires 512a and 512b, the proxy cable wires 513a and 513b, and the illumination system 1101 are exemplarily illustrated in FIG. 11. The optical imaging system 112 is illustrated in FIG. 1 and FIG. 2. The principal cable wires 512a and 512b and the proxy cable wires 513a and 513b are illustrated in FIGS. 5A-5B. In FIG. 11, the principal cable wire 512a is hidden behind the working channel 1102 and is therefore not visible. The operator may pull on one principal cable wire 512a and push on the other principal cable wire 512b, thus causing the flexible distal end 105a of the shaft assembly 102a to deflect a controlled amount. The amount of deflection is determined by the diameter of the shaft assembly 102a and the amount of linear movement of the principal cable wires 512a and 512b within the body of the shaft assembly 102a. For example, a small-diameter shaft assembly may require less linear movement of the principal cable wires 512a and 512b than a large-diameter shaft assembly for the same amount of deflection of the flexible distal end 105a of the shaft assembly 102a.

The shaft assembly 102a may also incorporate a working channel 1102 as exemplarily illustrated in FIG. 11. The shaft assembly 102a comprises a flexible insertion shaft 105 with a deflecting and bending section. The flexible distal end 105a of the flexible insertion shaft 105 corresponds to the deflecting and bending section of the flexible insertion shaft 105.

The portable endoscope 100 further comprises an internal cable wire control system 514 integrated with the detachable operator control section assembly 101, as exemplarily illustrated in FIGS. 5A-5B. The internal cable wire control system 514 controls orientation and angular position of the flexible distal end 105a of the shaft assembly 102a. The internal cable wire control system 514 may manipulate movements of the deflecting and bending section of the flexible insertion shaft 105 to control the orientation and the angular position of the flexible distal end 105a. The internal cable wire control system 514 utilizes a two way or a four way cable wire configuration for controlling the orientation and the angular position of the flexible distal end 105a. The two way cable wire configuration controls the upward and downward movements of flexible distal end 105a. The four way cable wire configuration controls the upward, downward, left side and right side movements of the flexible distal end 105a.

The internal cable wire control system 514 utilizes an adaptable drive transmission system 500 to control the orientation and angular position of the flexible distal end 105a for each of the shaft assemblies 102a, 102b, and 102c using the principal cable wires 512a and 512b, or the proxy cable wires 513a and 513b. The portable endoscope 100 further comprises a cable wire switch 110 integrated with the shaft assembly 102a, illustrated in FIG. 1, for engaging, disengaging, or dissociating the principal cable wires 512a and 512b, or the proxy cable wires 513a and 513b with the adaptable drive transmission system 500.

Since the portable endoscope 100 may be attached to different flexible insertion shafts 105, each with potentially unique pull requirements, the detachable operator control section assembly 101 senses or reads the requirements for the flexible insertion shaft 105 being attached and adjusts the gearing and leverage so that the entire range of thumb motion of the operator controlling the steering lever 103 is used for the entire range of steering deflection.

The adaptable drive transmission system 500 automatically selects the range of deflection of the flexible distal end 105a of the shaft assembly 102a and automatically adapts to differences in diameter of the different shaft assemblies 102a, 102b, and 102c. The operator may select shaft assemblies 102a, 102b, and 102c so that a deflection input by the operator results in a similar deflection of the flexible distal end 105a of any shaft assembly 102a, 102b, or 102c, regardless of the diameter of the selected shaft assembly 102a. In addition, the operator may select different ranges of deflection for shaft assemblies 102a, 102b, and 102c of the same diameter.

Without the adaptable drive transmission system 500, the detachable operator control section assembly 101 would need to be set for the largest possible output to control the largest endoscope. Setting the detachable operator control section assembly 101 for the largest possible output may lead to a disproportionate deflection of a small endoscope by the slightest movement of the steering lever 103. Alternatively, the detachable operator control section assembly 101 would need to be set for the smallest possible output to control small endoscopes. Setting the detachable operator control section assembly 101 for the smallest possible output may lead to a circumstance where a large endoscope will not deflect fully. The large endoscope may only be deflected to a half-way point, which may be unacceptable to the operator. The adaptable drive transmission system 500 allows the automatic changing of the output according to the endoscope assembled by the operator. Hence, for a small endoscope, the adaptable drive transmission system 500 adjusts for small deflections. Similarly, for a large endoscope, the adaptable drive transmission system 500 adjusts for large deflections.

Figure 6:
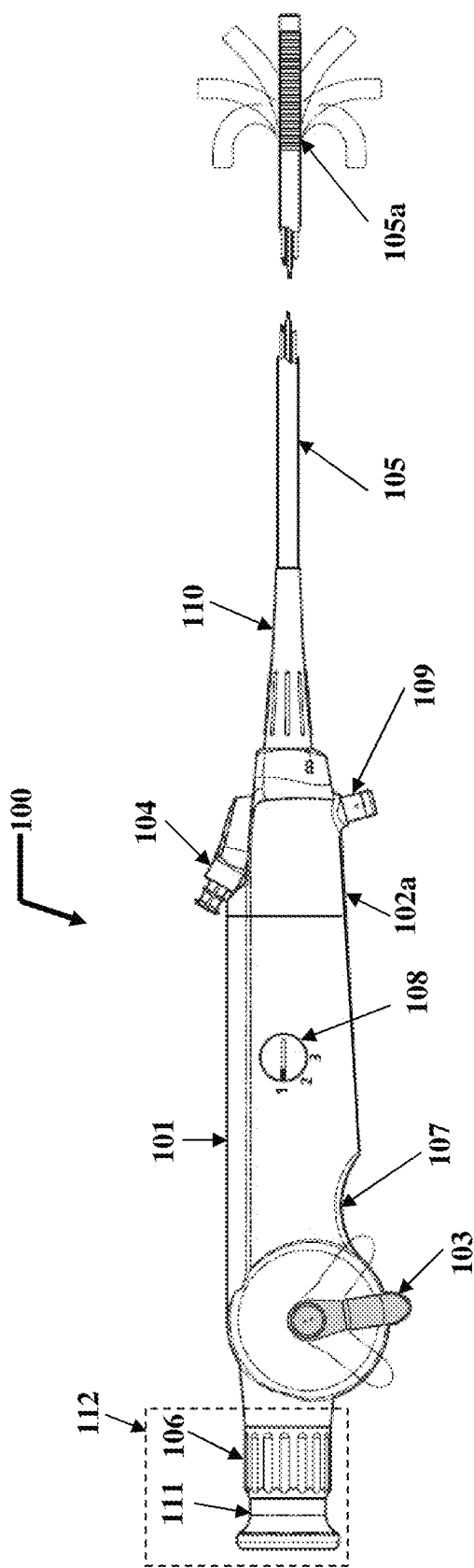
FIG. 6 exemplarily illustrates flexible distal end movements of a portable endoscope corresponding to movements of a steering lever of the portable endoscope.

The internal cable wire control system 514 comprises a steering lever 103 for controlling angular movements of the flexible distal end 105a of each of the shaft assemblies 102a, 102b, and 102c as exemplarily illustrated in FIG. 6. The steering lever 103 manipulates movement of the principal cable wires 512a and 512b, or the proxy cable wires 513a and 513b based on the engagement of the principal cable wires 512a and 512b, or the proxy cable wires 513a and 513b with the adaptable drive transmission system 500. The steering lever 103 may be adjusted to obtain a predefined degree of angular movements of the flexible distal end 105a ranging from about 0 degrees to about 270 degrees.

In order to steer and deflect the flexible distal end 105a of the flexible insertion shaft 105, the steering lever 103 is moved to pull the principal cable wires 512a and 512b, or proxy cable wires 513a and 513b within the shaft assembly 102a on either side of the deflecting and bending section of the flexible insertion shaft 105. The amount of pull necessary to effect the deflection of the flexible distal end 105a is directly proportional to the amount of the deflection required during a medical procedure and the dimensional specifications of the flexible insertion shaft 105. The amount of deflection of the flexible distal end 105a may vary depending on the dimensional specifications of the flexible insertion shaft 105 and the medical procedure. An operator may utilize a range of motions of the steering lever 103 to control the amount of deflection of the flexible distal end 105a. The range of motions of the steering lever 103 may enhance sensitivity of control of the flexible distal end 105a during a medical procedure and facilitate use of complete range of deflection of the flexible distal end 105a.

The adaptable drive transmission system 500 converts the motion of the steering lever 103 to linear movements of the principal cable wires 512a and 512b, or the proxy cable wires 513a and 513b. The adaptable drive transmission system 500 comprises an angulation and deflection gear system 502 with gears and gear track subassemblies for matching operator input to scope steering output of the portable endoscope 100, as exemplarily illustrated in FIG. 5A. The neutral lock-out system and the quick disconnect sub-assembly facilitate engagement or disengagement of the principal cable wires 512a and 512b, or the proxy cable wires 513a and 513b with the internal cable wire control system 514 using the control switch. The adaptable drive transmission system 500 further comprises a shifter rod 504, a shifter plate 501, a return spring 503, a connecting rod 506, and a crank lever 505 as illustrated in FIGS. 5A-5C. An angular displacement of the steering lever 103 translates into angular movement of the crank lever 505. The angular movement of the crank lever 505 translates into linear movement of the connecting rod 506. The amount of linear displacement depends upon the rotational position of the shifter plate 501.

The shifter rod 504 connects the proximal end of the shaft assembly 102a with the detachable operator control section assembly 101. The length of the shifter rod 504 is dependent on cable wire requirements for a particular shaft assembly 102a attached to the detachable operator control section assembly 101, which depends on the medical procedure. The shifter rod 504 makes contact with the angulation and deflection gear system 502 using a rack and pinion drive system 507.

A rack and pinion drive is typically a gearing mechanism in which a pair of gears converts rotational motion into linear motion or vice-versa. Linear motion of the shifter rod 504 is translated by the circular pinion on the back of the shifter plate 501 into rotational motion of the shifter plate 501. Further, the swing of the crank lever 505 is converted into linear motion of the connecting rod 506, which in turn rotates a gear cluster 1501 of the rack and pinion drive system 507. The rotation of the gear cluster 1501 is converted into linear motion of a pair of reciprocating racks 510. The reciprocating racks 510 comprise a top driven rack subassembly 510a and a bottom driven rack subassembly 510b. The cable wire anchor boxes 508 connected to the ends of the reciprocating racks 510 then pull on the principal cable wires 512a and 512b or the proxy cable wires 513a and 513b, depending on which principal cable wires 512a and 512b and the proxy cable wires 513a and 513b are engaged.

The angulation and deflection gear system 502 rotates a shifter plate 501. The amount of the rotation of the shifter plate 501 depends on the length of the shifter rod 504. The shifter plate 501 comprises a spiral cam path for a pivot pin 509 through the end of the connecting rod 506 to traverse the spiral cam path corresponding to the rotation of the shifter plate 501. The crank lever 505 is also connected to the pivot pin 509. When the shifter plate 501 is rotated, the pivot pin 509 may be raised or lowered relative to the central axis of rotation of the adaptable drive transmission system 500. The position of the shifter plate 501 defines the length of the crank lever arm of the crank lever 505.

When the pivot pin 509 exemplarily illustrated in FIG. 5B traverses the spiral cam path, the position of the pivot pin 509 relative to the central axis of the crank lever 505 changes along the spiral cam path. The closer the pivot pin 509 is to the central axis, the shorter is the effective arm length of the crank lever 505 acting upon the connecting rod 506. Conversely, the farther the pivot pin 509 is from the central axis, the longer is the effective arm length of the crank lever 505 acting upon the connecting rod 506. The shorter the effective arm length is the smaller is the overall linear travel of the connecting rod 506. Conversely, the longer the effective arm length is, the greater is the overall linear travel of the connecting rod 506.

The steering lever 103 may be rigidly attached to the crank lever 505. As the steering lever 103 is moved forward and aft, the crank lever 505 drives the connecting rod 506 aft and forward by a proportional amount. The distal end of the connecting rod 506 is in contact with the rack and pinion drive system 507. The movement of the connection rod 506 in turn causes a pair of reciprocating racks 510 to create a push-pull effect. The distal ends of the paired reciprocating racks 510 carry cable wire anchor boxes 508. The cable wire anchor boxes 508 may house multiple cable wire anchors 1103 as illustrated in FIG. 11. The cable wire anchor boxes 508 interface directly with the principal cable wires 512a and 512b, or the proxy cable wires 513a and 513b resulting in the deflection at the flexible distal end 105a of the shaft assembly 102a. When the flexible insertion shaft 105 is detached from the detachable operator control section assembly 101, the return spring 503 resets the position of the angulation and deflection gear system 502 to a preset initial position.

To use the portable endoscope 100, the cable wire switch 110 may be moved to engage the principal cable wires 512a and 512b, or proxy cable wires 513a and 513b with the adaptable drive transmission system 500. The cable wire switch 110 may then be used to engage, for example, the principal cable wires 512a and 512b with the adaptable drive transmission system 500. On engagement of the principal cable wires 512a and 512b, the adaptable drive transmission system 500 secures the angulation and deflection gear system 502 with the shaft assembly 102a, as exemplarily illustrated in FIG. 5A. The steering lever 103 may then be used to control the angular movements of the flexible distal end 105a of the shaft assembly 102a.

The internal cable wire control system 514 utilizes the proxy cable wires 513a and 513b for controlling the flexible distal end 105a of the shaft assembly 102a in an event of failure of the principal cable wires 512a and 512b during a medical procedure in progress. In the event of the failure of the principal cable wires 512a and 512b, the cable wire switch 110 disengages the principal cable wires 512a and 512b from the adaptable drive transmission system 500 and engages the proxy cable wires 513a and 513b with the adaptable drive transmission system 500. The internal cable wire control system 514 may then utilize the proxy cable wires 513a and 513b for controlling the orientation and the angular movements of the flexible distal end 105a. The immediate engagement of the proxy cable wires 513a and 513b for use in an event of failure of the principal cable wires 512a and 512b may improve procedure completion rates and usability of the portable endoscope 100. The principal cable wires 512a and 512b and the proxy cable wires 513a and 513b may be protected by multiple cable sheaths 1105, as exemplarily illustrated in FIG. 11.

The portable endoscope 100 may further comprise a safety switch 108 integrated with the detachable operator control section assembly 101, as exemplarily illustrated in FIG. 1. The safety switch 108 in a first operational position may allow normal operation of the portable endoscope 100 when the shaft assembly 102a is attached to the detachable operator control section assembly 101. The safety switch 108 in a second operational position or a "neutral lockout" position may set the adaptable drive transmission system 500 in a neutral safety position and allow actuation of the cable wire switch 110 to disengage the principal cable wires 512a and 512b, or the proxy cable wires 513a and 513b from the adaptable drive transmission system 500. The safety switch 108 in a third operational position may allow detachment of the shaft assembly 102a from the detachable operator control section assembly 101 without damaging the internal mechanisms and internal components of the portable endoscope 100.

In the event of failure of the principal cable wires 512a and 512b during a medical procedure in progress, the safety switch 108 may first be set to the "neutral lockout" position, thus locking the adaptable drive transmission system 500 in the neutral position. The cable wire switch 110 may then be rotated 90 degrees clockwise to disengage and dissociate the principal cable wires 512a and 512b from the adaptable drive transmission system 500. The control rod tabs corresponding to the principal cable wires 512a and 512b are disengaged from the cable wire anchor boxes 508. The control rod tabs corresponding to the principal cable wires 512a and 512b are engaged with fixed pockets provided within the chassis sub-assembly 1201. The control rod tabs corresponding to the proxy cable wires 513a and 513b are engaged with the cable wire anchor boxes 508 vacated by the principal cable wires 512a and 512b. The operator then resets the safety switch 108 to the first operational position and may continue using the portable endoscope 100 with the proxy cable wires 513a and 513b.

The safety switch 108 sets the adaptable drive transmission system 500 in the neutral safety position prior to facilitating the disengagement and the dissociation of the principal cable wires 512a and 512b. The adaptable drive transmission system 500 may then be engaged with the proxy cable wires 513a and 513b using the cable wire switch 110. An operator, for example, a physician, may then continue to use the portable endoscope 100 with the proxy cable wires 513a and 513b engaged resulting in minimal interruption of the medical procedure. The proxy cable wires 513a and 513b may also be engaged with the adaptable drive transmission system 500 for use in place of the principal cable wires 512a and 512b without limitation to the use of the proxy cable wires 513a and 513b corresponding to the failure of the principal cable wires 512a and 512b.

Figure 7:
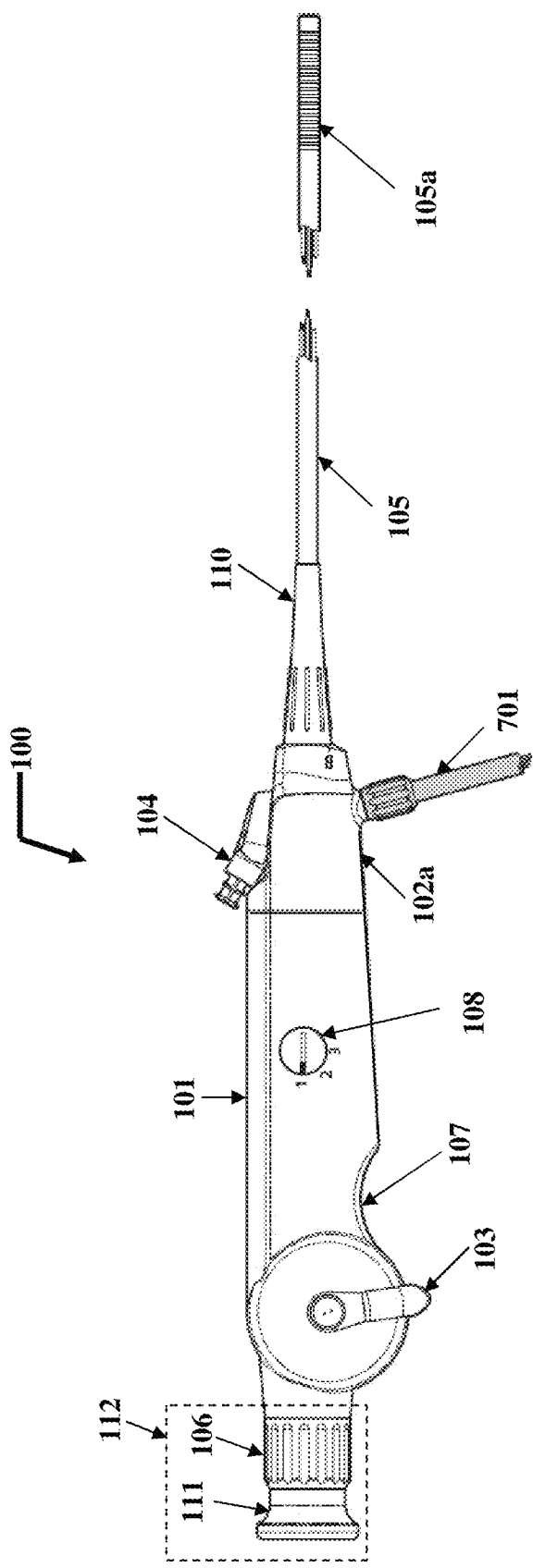
FIG. 7 exemplarily illustrates a portable endoscope with a light cable connected to the lighting channel.

The portable endoscope 100 further comprises an external light source in communication with the illumination system 1101 and the optical imaging system 112. The external light source provides light to the illumination system 1101 and the optical imaging system 112 of the portable endoscope 100. Multiple fiber optic bundles may be used as optical illumination cables in the illumination system 1101. The fiber optic bundle emits light from the flexible distal end 105a of the shaft assembly 102a on illumination. The shaft assembly 102a may be provided with a lighting channel 109 to facilitate the communication of the external light source with the illumination system 1101 and the optical imaging system 112. The external light source may comprise a remote light box in communication with the illumination system 1101 and the optical imaging system 112 through a light cable 701 connected to the lighting channel 109 as exemplarily illustrated in FIG. 7. The remote light box may, for example, be an alternating current powered high lumen output unit.

Figure 8:
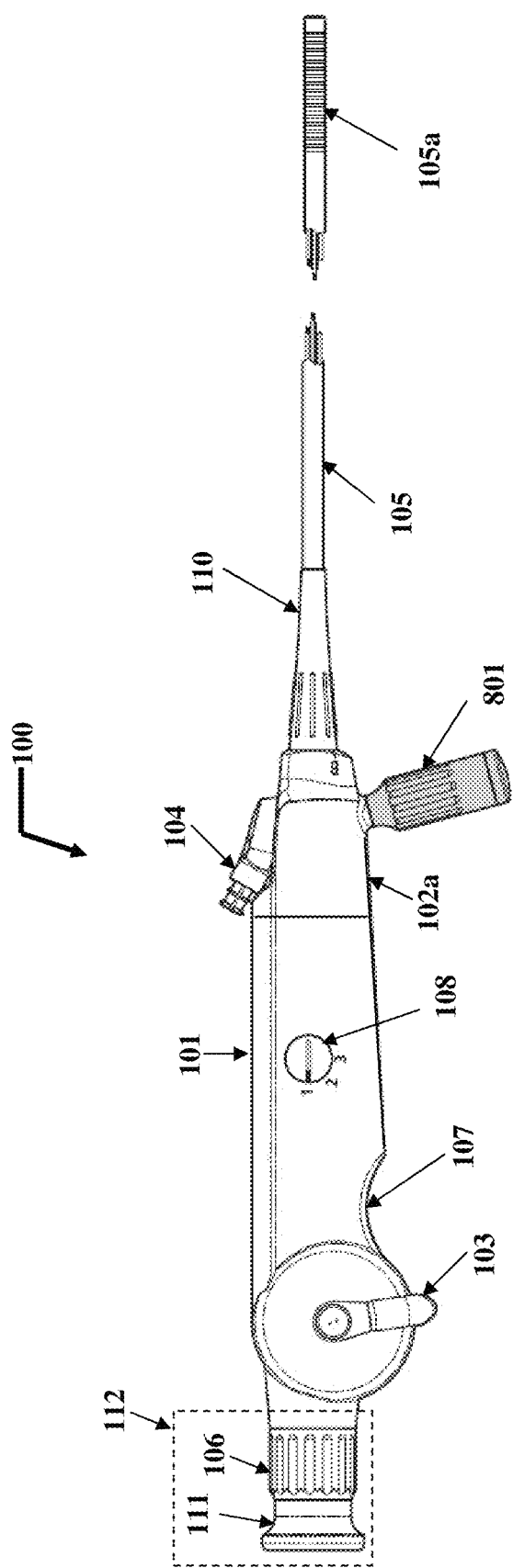
FIG. 8 exemplarily illustrates a portable endoscope with a light stick connected to the lighting channel.

The external light source may also comprise a detachable and portable light stick 801 connected to the lighting channel 109 as exemplarily illustrated in FIG. 8. The detachable and portable light stick 801 is a battery powered flashlight used to provide light energy to the illumination system 1101 and the optical imaging system 112 directly through the lighting channel 109. The detachable and portable light stick 801 eliminates the use of external electrical connecting cords and the external light cables for providing light to the portable endoscope 100. The detachable and portable light stick 801 facilitates freedom of movement of the portable endoscope 100 by an operator during a medical procedure.

The optical imaging system 112 integrated with the portable endoscope 100 captures and transmits visual information, for example, images, received from the shaft assembly 102a, of body regions scanned or accessed by the portable endoscope 100. The optical imaging system 112 may utilize the illumination system 1101 for illumination during the capture and transmission of the visual images. The optical imaging system 112 receives visual information of the body regions illuminated by the illumination system 1101 from the illumination cables of the illumination system 1101.

The optical imaging system 112 may comprise a standard eyepiece 111 for viewing the visual images gathered by an optical objective lens system provided at the flexible distal end 105a. The visual images gathered by the optical objective lens system are transmitted to the standard eyepiece 111 via a fiber optic cable through the flexible insertion shaft 105. The optical imaging system 112 comprises an optical focus mechanism. The optical focus mechanism may be provided on the detachable operator control section assembly 101, or the shaft assembly 102a. The optical focus mechanism utilizes a focus ring 106 to adjust optical focus of the optical imaging system 112. The focus ring 106 adjusts the optical focus of the visual images captured or transmitted from the shaft assembly 102a to the standard eyepiece 111 of the optical imaging system 112.

The flexible distal end 105a of the shaft assembly 102a comprises varied optical layout configurations of the optical objective lens system and different illumination outputs. In order to capture the visual images captured or transmitted to the standard eyepiece 111, a digital or an analog camera may be placed in communication with the standard eyepiece 111. The optical imaging system 112 further comprises an image bundle 511 as illustrated in FIGS. 5A-5B and FIG. 11, for transmitting the captured visual images from the flexible distal end 105a of the shaft assembly 102a to the standard eyepiece 111. The image bundle 511 may be a fiber optic image bundle. The image bundle 511 may also be a videoscope.

The portable endoscope 100 further comprises an image capturing system integrated with the detachable operator control section assembly 101. The image capturing system may comprise image sensors provided at the flexible distal end 105a of the shaft assembly 102a and a visual display unit 901. The image sensors may comprise a charged coupled device (CCD), a complementary metal oxide semiconductor (CMOS) image sensor, or a contact image sensor (CIS). The visual display unit 901 may be detachably attached to the detachable operator control section assembly 101. The images sensors capture and transmit the visual images to the visual display unit 901. The visual images captured by the image sensors are converted into an electric signal and then transmitted to the visual display unit 901.

The visual display unit 901 then displays the captured and transmitted visual images. For example, the detachable operator control section assembly 101 and the shaft assembly 102a provided with a CCD chip as an image sensor may be used as a "hybrid video-fiberscope" for capturing video content on the portable endoscope 100. The hybrid video-fiberscope may be an alternative to a dedicated videoscope which requires the external cords or the cables connected to an external display unit 901 for capturing the video content through the dedicated videoscope.

Figure 9A:
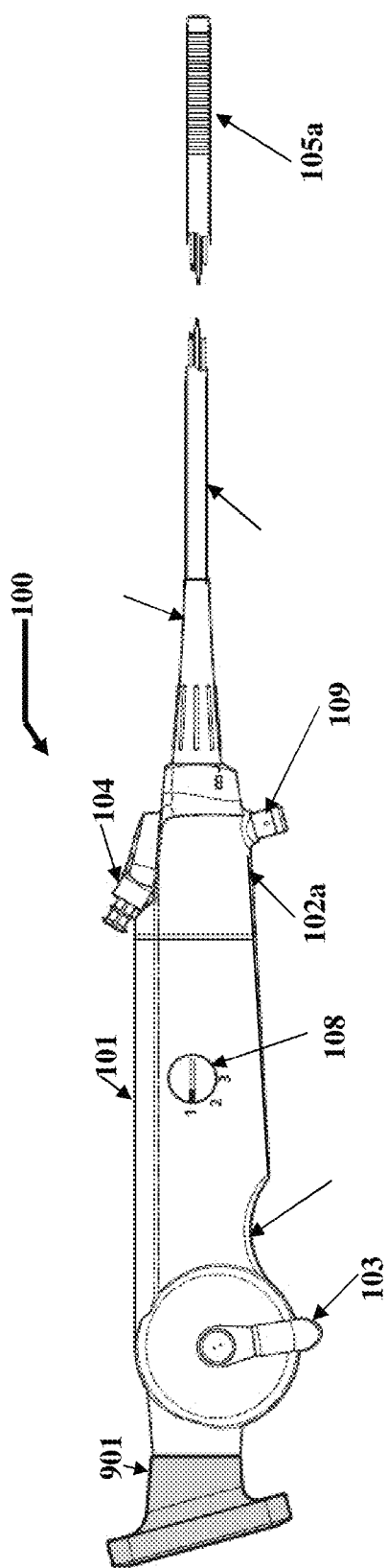
FIGS. 9A-9B exemplarily illustrate a portable endoscope fitted with a portable visual display unit.
Figure 9B:
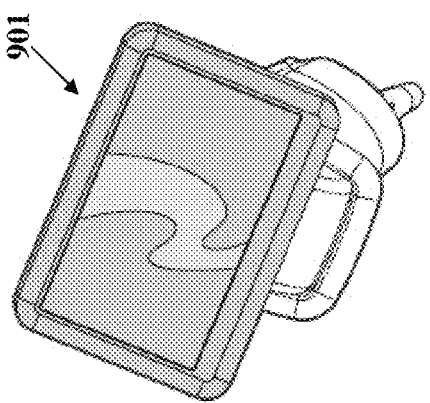

The hybrid video-fiberscope may also be an alternative to a fiberscope. Typically, the fiberscope comprises an external video camera converter attached to a standard eyepiece 111 of the fiberscope. The external cords or the cables may need to be connected to the fiberscope from the external video camera converter to capture the video content. The hybrid video-fiberscope may comprise an image capturing device integrated with the flexible distal end 105a of the shaft assembly 102a to capture the video image content. The detachable operator control section assembly 101 of the hybrid video-fiberscope with an integrated portable visual display unit 901 may be used to display the video content as illustrated in FIGS. 9A-9B. The image capturing system may also be provided with an optional visual display unit 901 detachably attached to the detachable operator control section assembly 101 for displaying the captured and transmitted images received from the image capturing system. The visual images may also be displayed on an external visual display unit 901 by wired or a wireless communication.

The portable endoscope 100 may further comprise a working channel 1102 facilitated through the shaft assembly 102a and a working channel turret 104 integrated with the shaft assembly 102a. The working channel turret 104 provides access to the working channel 1102 within the shaft assembly 102a and aids different medical procedures, for example, lavage, aspiration, biopsy, or manipulation. The operator, for example, a physician, may use the working channel turret 104 to lavage field of view in the optical imaging system 112, or the image capturing system, aspirate fluids and debris, insert tools for manipulation of tissues or structures, and collect biological body samples for biopsy. The working channel turret 104 may be provisioned to rotate laterally in order to facilitate left handed and right handed use of the portable endoscope 100. Internal components of the flexible insertion shaft bundle 1100 with the working channel 1102 are exemplarily illustrated in FIG. 11. As illustrated in FIG. 11, the internal components of the portable endoscope 100 are protected by an endoscope sheath 1104. FIG. 11 further illustrates a ferrule 1106 which is used to attach the flexible insertion shaft bundle 1100 within the shaft assembly 102a.

Figure 10:
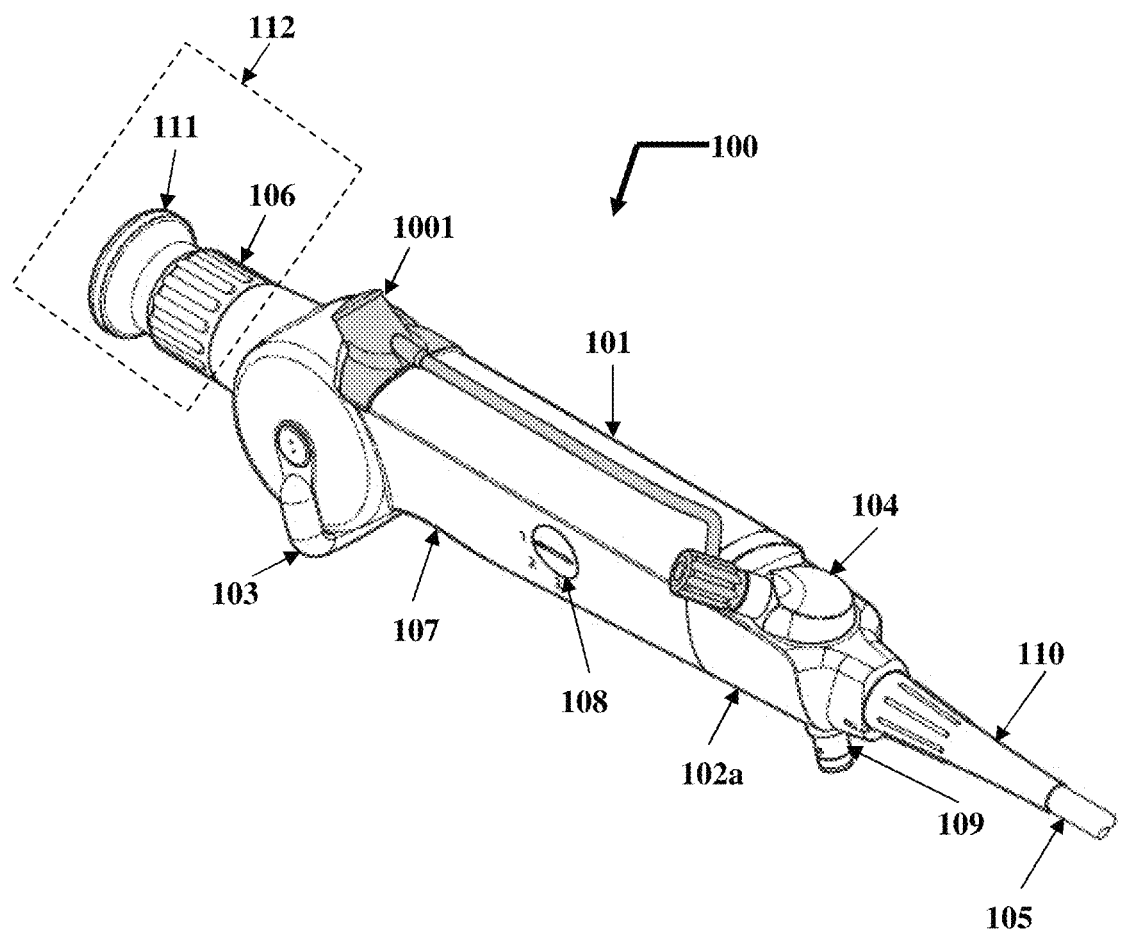
FIG. 10 exemplarily illustrates a portable endoscope fitted with a flow control valve.

A suction and irrigation control system in communication with the working channel turret 104 and the working channel 1102 may be used in medical lavage or aspiration procedures and may be employed simultaneously along with the portable endoscope 100. The suction and irrigation control system may be detachably attached to the detachable operator control section assembly 101 and affixed to the working channel turret 104 provided on the shaft assembly 102a. The suction and irrigation control system may comprise a flow control valve 1001 affixed to the working channel turret 104 provided on the shaft assembly 102a as illustrated in FIG. 10. The flow control valve 1001 may be connected to the working channel turret 104 via a flexible tubing to accommodate the lateral rotary movement of the working channel turret 104. The flow control valve 1001 may be used to control flow of fluids and air within the working channel 1102 during the medical lavage or aspiration procedure. The suction and irrigation control system may also remove body fluids. Components of the suction and irrigation control system such as a cylinder base, internal tubings and fittings may be detachable from the portable endoscope 100.

Figure 12:
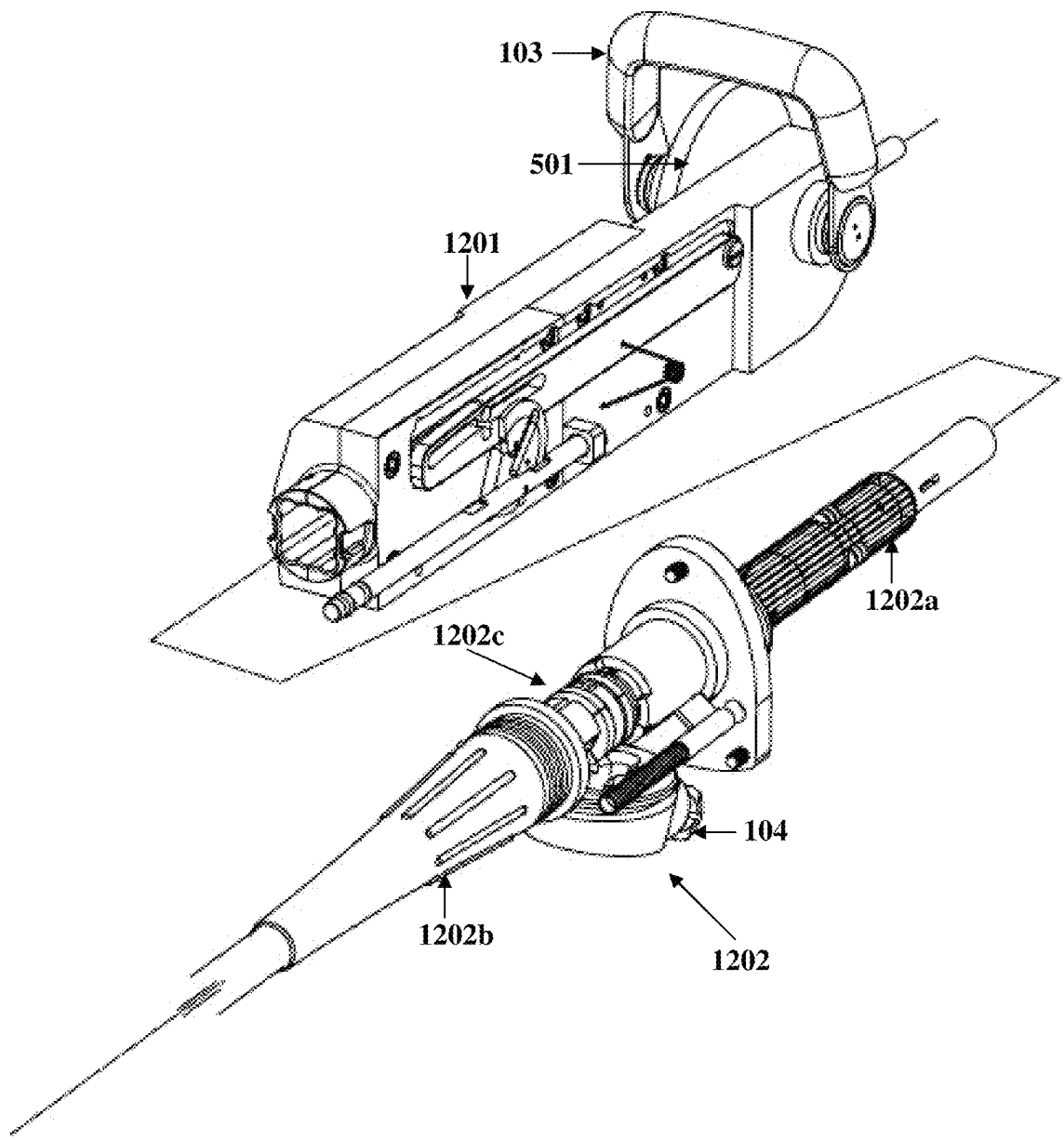
FIG. 12 exemplarily illustrates a detachable operator control section assembly and a detachable and interchangeable shaft assembly of a portable endoscope for diverse medical disciplines and associated medical procedures without an external housing.
Figure 18:
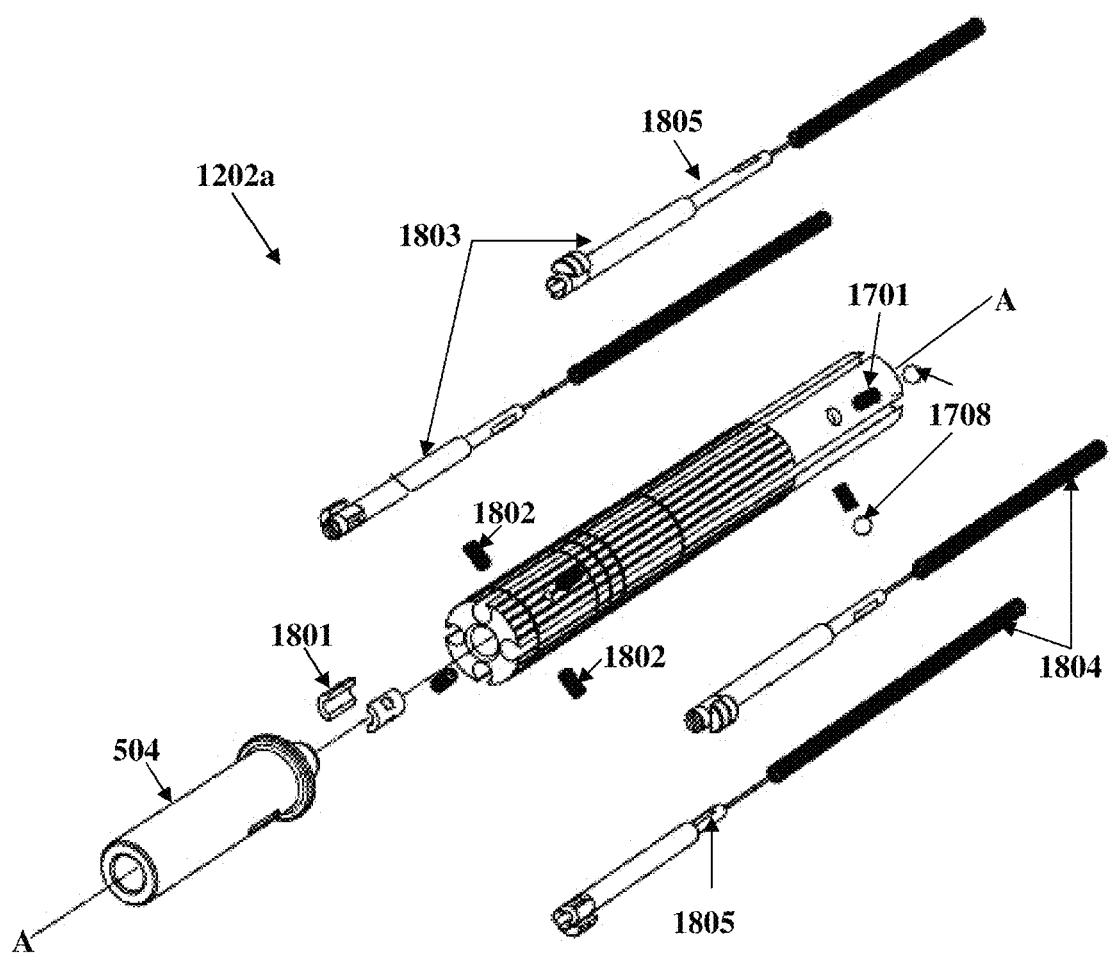
FIG. 18 exemplarily illustrates an exploded view of the proximal extreme section of the post subassembly at the proximal end of the detachable and interchangeable flexible insertion shaft assembly.

FIG. 12 exemplarily a detachable operator control section assembly 101 and a shaft assembly 102a of the portable endoscope 100 for diverse medical disciplines and associated medical procedures without an external housing. FIG. 12 illustrates a chassis subassembly 1201 and a post subassembly 1202. The post subassembly 1202 comprises a proximal extreme section 1202a, a frontal section 1202b, and a mid proximal section 1202c. FIG. 18 exemplarily illustrates an exploded view of the proximal extreme section 1202a of the post subassembly 1202. The proximal extreme section 1202a of the post subassembly 1202 comprises the shifter rod 504, multiple image bundle collets 1801, multiple collet set screws 1802, multiple control rod subassemblies 1803, multiple neutral springs 1804, multiple neutral lockout (NLO) balls 1708, and multiple NLO springs 1701.

The image bundle collets 1801 center the image bundle 511, using the collet set screws 1802, on the central axis of the post subassembly 1202 at the proximal end of the shaft assembly 102a. The control rod subassemblies 1803 create anchors at the proximal ends of the cable wires that are used to steer or deflect the flexible distal end 105a of the shaft assembly 102a, so that the cable wires may easily be grasped by the adaptable drive transmission system 500. The control rod subassemblies 1803 also enable fine-tune adjusting of cable wire length using a telescoping screw 1805. The neutral springs 1804 act upon the cable wire anchors 1103 to return the cable wires to a neutral position within the adaptable drive transmission system 500. The NLO balls 1708 and the NLO springs 1701 together form a detent for rotation of the post subassembly 1202. The proximal extreme section 1202a of the post subassembly 1202 attaches to the mid proximal section 1202c of the post subassembly 1202 along the axis A-A illustrated in FIG. 18.

Figure 19:
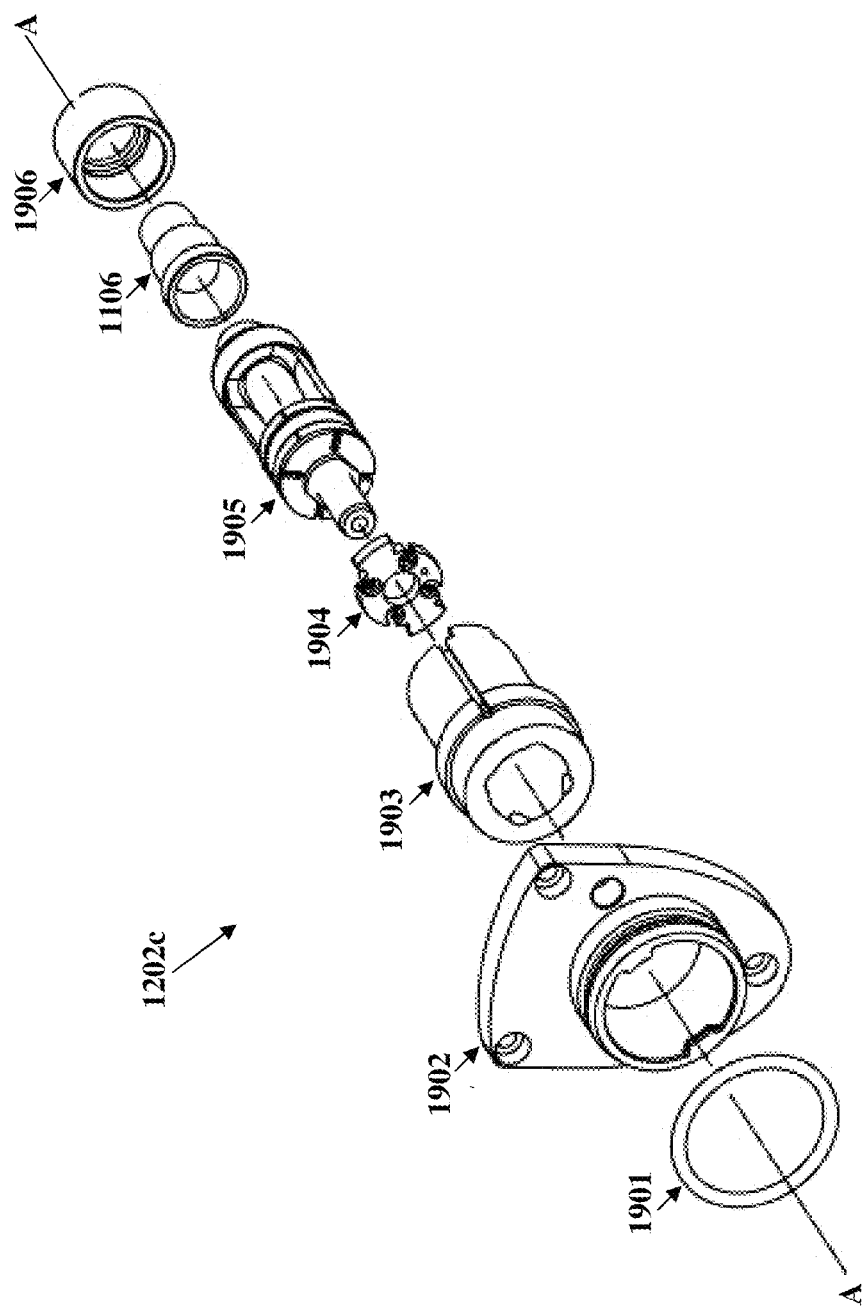
FIG. 19 exemplarily illustrates an exploded view of the mid proximal section of the post subassembly at the proximal end of the detachable and interchangeable flexible insertion shaft assembly.

FIG. 19 exemplarily illustrates an exploded view of the mid proximal section 1202c of the post subassembly 1202. The mid proximal section 1202c of the post subassembly 1202 comprises an "O" shaped ring 1901, a locking collar 1902, a rotation stop 1903, a spring plate 1904, a sheath anchor subassembly 1905, the ferrule 1106, and a ferrule nut 1906. The "O" shaped ring 1901 creates a seal between the housings of the shaft assembly 102a and operator control section assembly 101 to maintain the sterility of the internal workings. The locking collar 1902 is the female portion of a quarter-turn bayonet connection for coupling the shaft assembly 102a to the operator control section assembly 101. The rotation stop 1903 limits rotation of the post subassembly 1202 during selection of the principal cable wires 512a and 512b or the proxy cable wires 513a and 513b. The spring plate 1904 acts as a backstop for the NLO springs 1701 that act upon the cable wire anchors 1103. The sheath anchor subassembly 1905 is used to fix the proximal ends of the cable sheaths 1105. The ferrule 1106 and the ferrule nut 1906 enable attachment of the flexible insertion shaft bundle 1100 (not shown in FIG. 19) of the shaft assembly 102a to the post subassembly 1202. The mid proximal section 1202c of the post subassembly 1202 attaches to the proximal extreme section 1202a of the post subassembly 1202 along the axis A-A illustrated in FIG. 19.

Figure 13A:
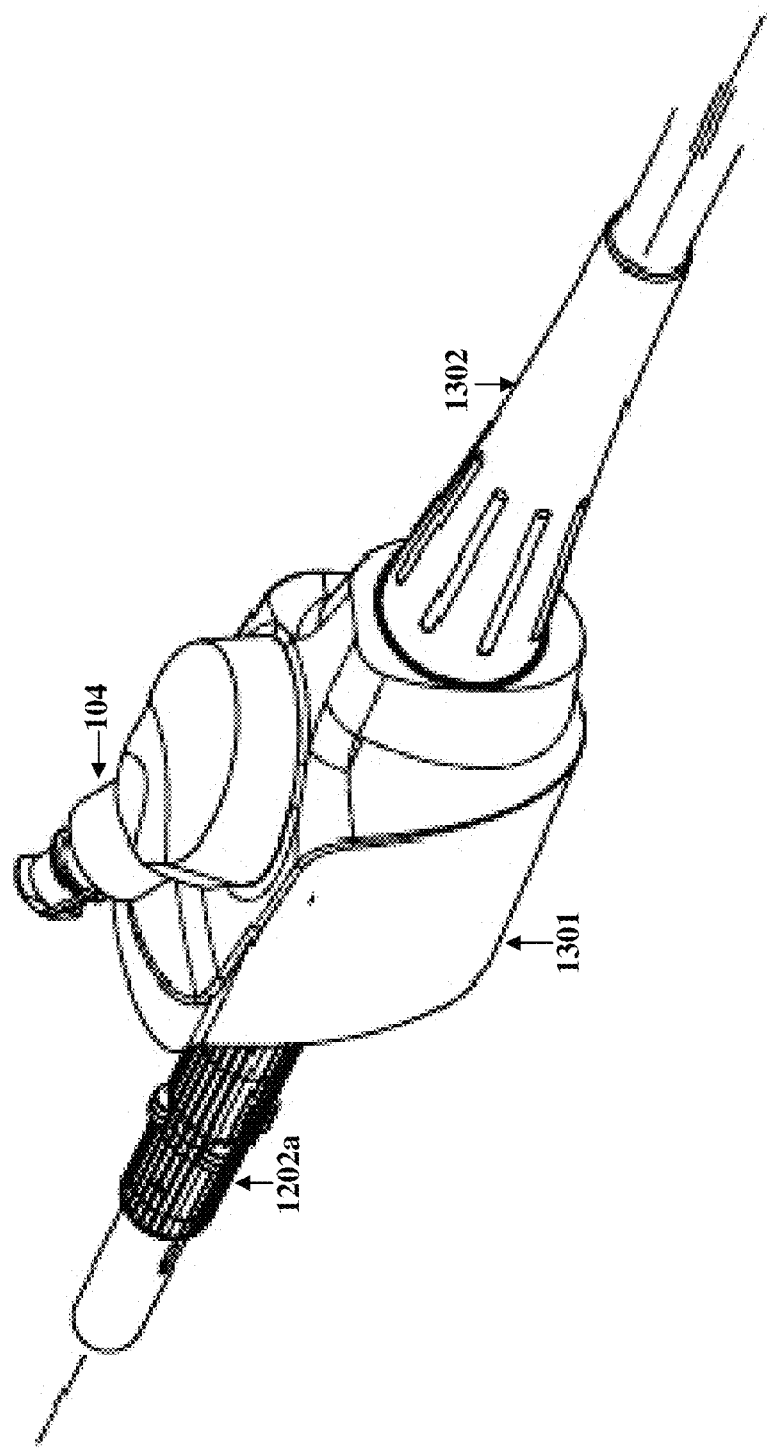
FIG. 13A exemplarily illustrates an isometric view of the proximal end of the quick disconnect subassembly.
Figure 13B:
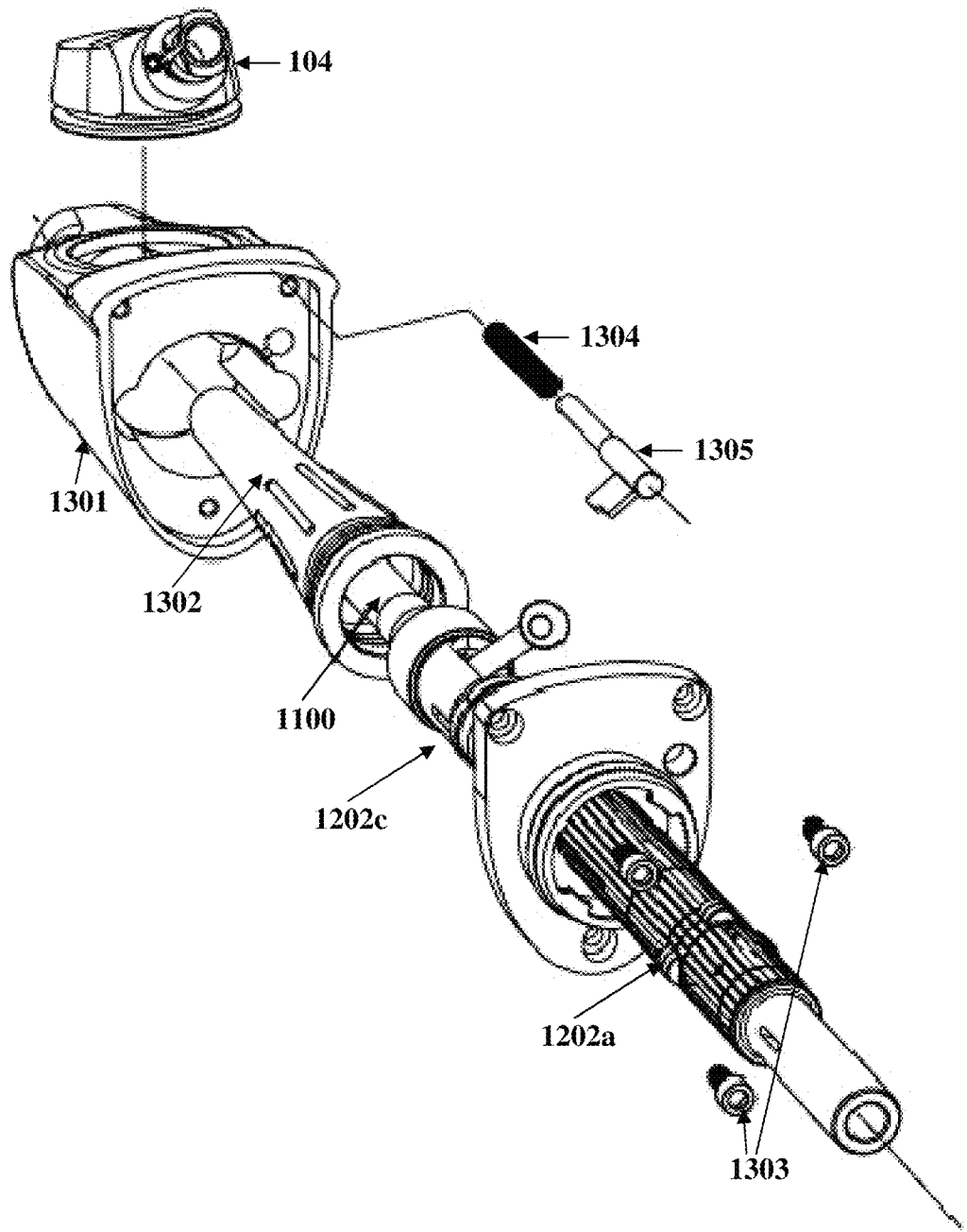
FIG. 13B exemplarily illustrates an exploded view of the proximal end of the quick disconnect subassembly of the detachable and interchangeable flexible insertion shaft assembly of the portable endoscope.

FIG. 13A exemplarily illustrates an isometric view of the proximal end of the quick disconnect subassembly of the portable endoscope 100. FIG. 13B exemplarily illustrates an exploded view of the quick disconnect subassembly. The quick disconnect subassembly comprises the working channel turret 104, a disconnect housing 1301, a rotation tip boot 1302, the flexible insertion shaft bundle 1100 portion of the shaft assembly 102a, a neutral lockout (NLO) key 1305, an NLO key spring 1304, and the post subassembly 1202. The NLO key spring 1304 is a return spring for the NLO key 1305.

The quick disconnect subassembly enables the shaft assembly 102a and operator control section assembly 101 to be connected or separated. The rotation tip boot 1302 forms a covering for sealing the sheath anchor subassembly 1905 and provides grip to enable rotation of the post subassembly 1202 for switching between the principal cable wires 512*a* and 512*b* and the proxy cable wires 513*a* and 513*b*. The NLO key 1305 controls position and engagement of the NLO balls 1708 and therefore ability to rotate the post subassembly 1202. The post subassembly 1202 provides tracks for controlling linear movement of the cable wire anchors 1103. Multiple bolts 1303 or other fastening means may be used to secure the different components of the quick disconnect assembly.

Figure 14:
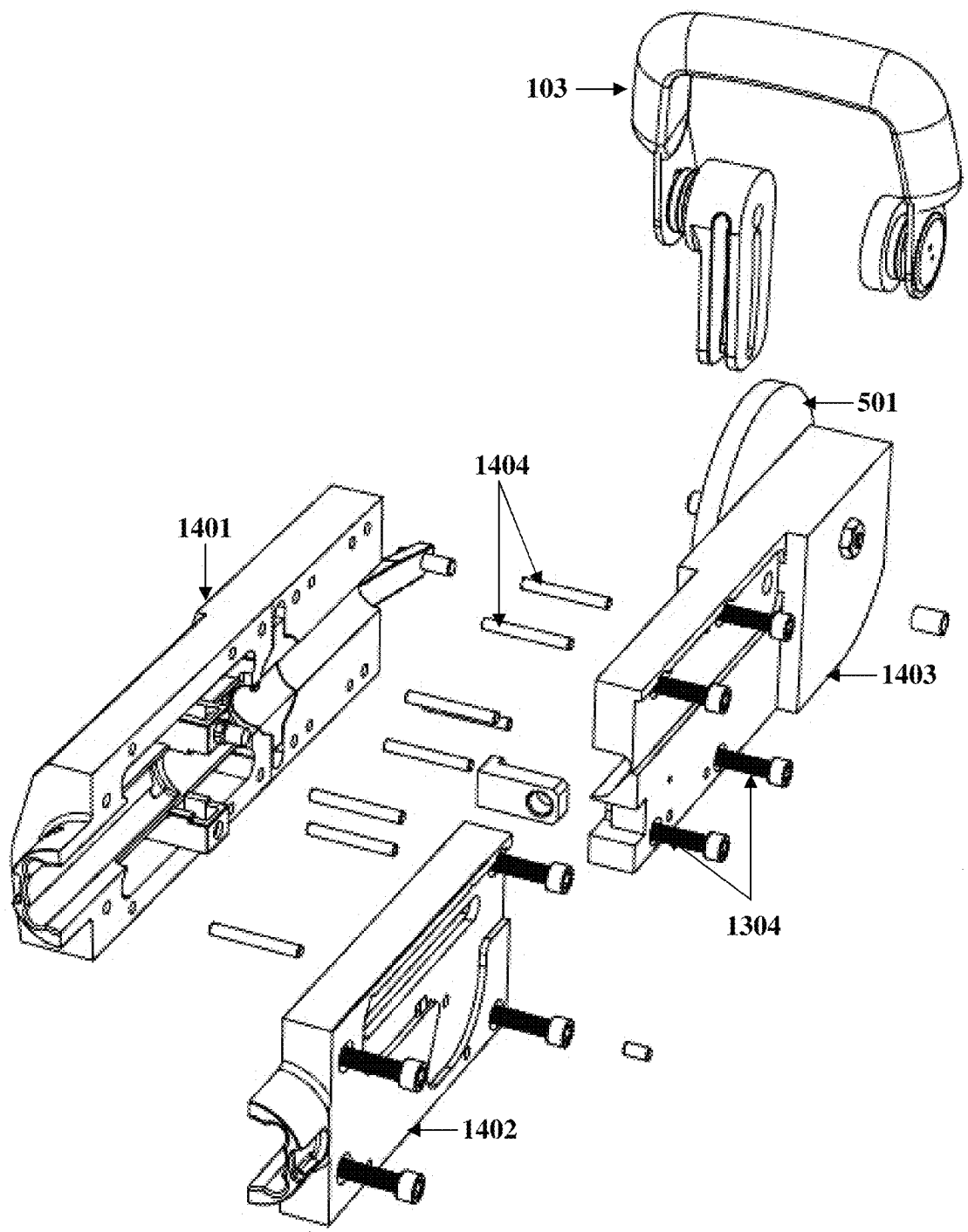
FIG. 14 exemplarily illustrates an exploded view of a chassis subassembly within the operator control section assembly.

FIG. 14 exemplarily illustrates an exploded view of the chassis subassembly 1201 within the operator control section assembly 101. The chassis subassembly 1201 comprises a main block 1401, a side block 1402, a tail block 1403, the shifter plate 501, and the steering lever 103. The chassis subassembly 1201 is made of the main block 1401, the side block 1402, and the tail block 1403 to enable the internal components to be machined and to allow for insertion of internal components. The chassis subassembly 1201 provides a structure within which the internal components function. The shifter plate 501 is used by the adaptable drive transmission system 500. The steering lever 103 is used by the operator to control the portable endoscope 100. The main block 1401, the side block 1402, and the tail block 1403 may be secured using multiple bolts 1303 and locating pins 1404, or other fastening means.

Figure 15:
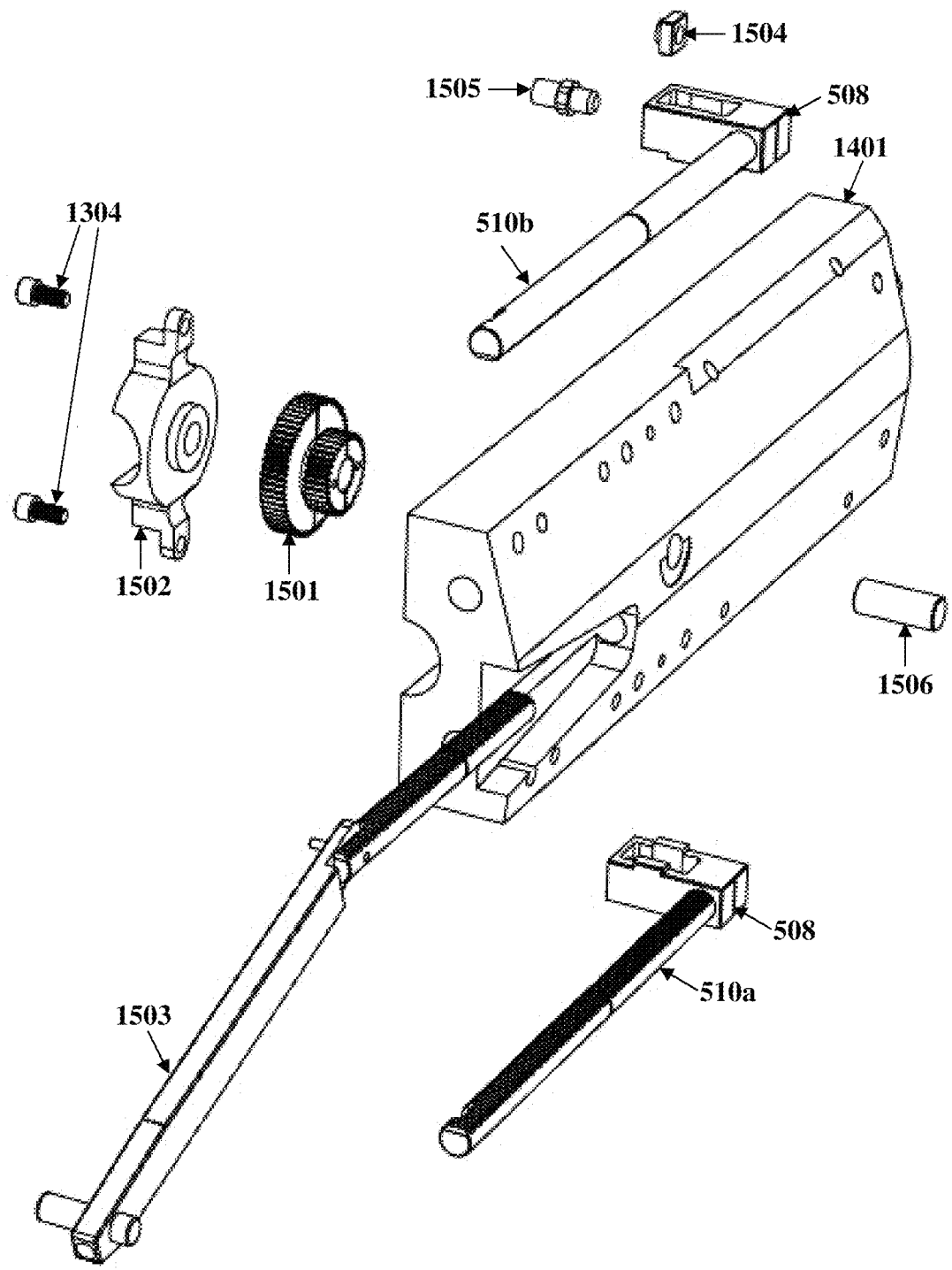
FIG. 15 exemplarily illustrates an exploded view of a main block of the chassis subassembly.

FIG. 15 exemplarily illustrates an exploded view of the main block 1401 of the chassis subassembly 1201. The main block 1401 comprises a gear cluster 1501, a gear cover 1502, a drive rack subassembly 1503, a bottom driven rack subassembly 510*b*, cable wire anchor boxes 508, and a top driven rack subassembly 510*a*. The gear cluster 1501 adds gain to the system to amplify the input from the drive rack subassembly 1503. The gear cover 1502 retains the gear cluster 1501 within the chassis subassembly 1201. The drive rack subassembly 1503 transfers linear movement of the connection rod 506 to the gear cluster 1501. The top driven rack subassembly 510*a* and the bottom driven rack subassembly 510*b* together are output shafts of the adaptable drive transmission system 500. The cable wire anchor boxes 508 enables connection of the cable wire anchors 1103 to the adaptable drive transmission system 500 via the top driven rack subassembly 510*a* and the bottom driven rack subassembly 510*b*. Secured to the top driven rack subassembly 510*a* may be an NLO post 1504 and a t-nut 1505 for interfacing the adaptable drive transmission system 500 to the neutral lock-out system. The main block 1401 further comprises a first axle 1506. The first axle 1506 acts as a pivot for the gear cluster 1501.

Figure 16:
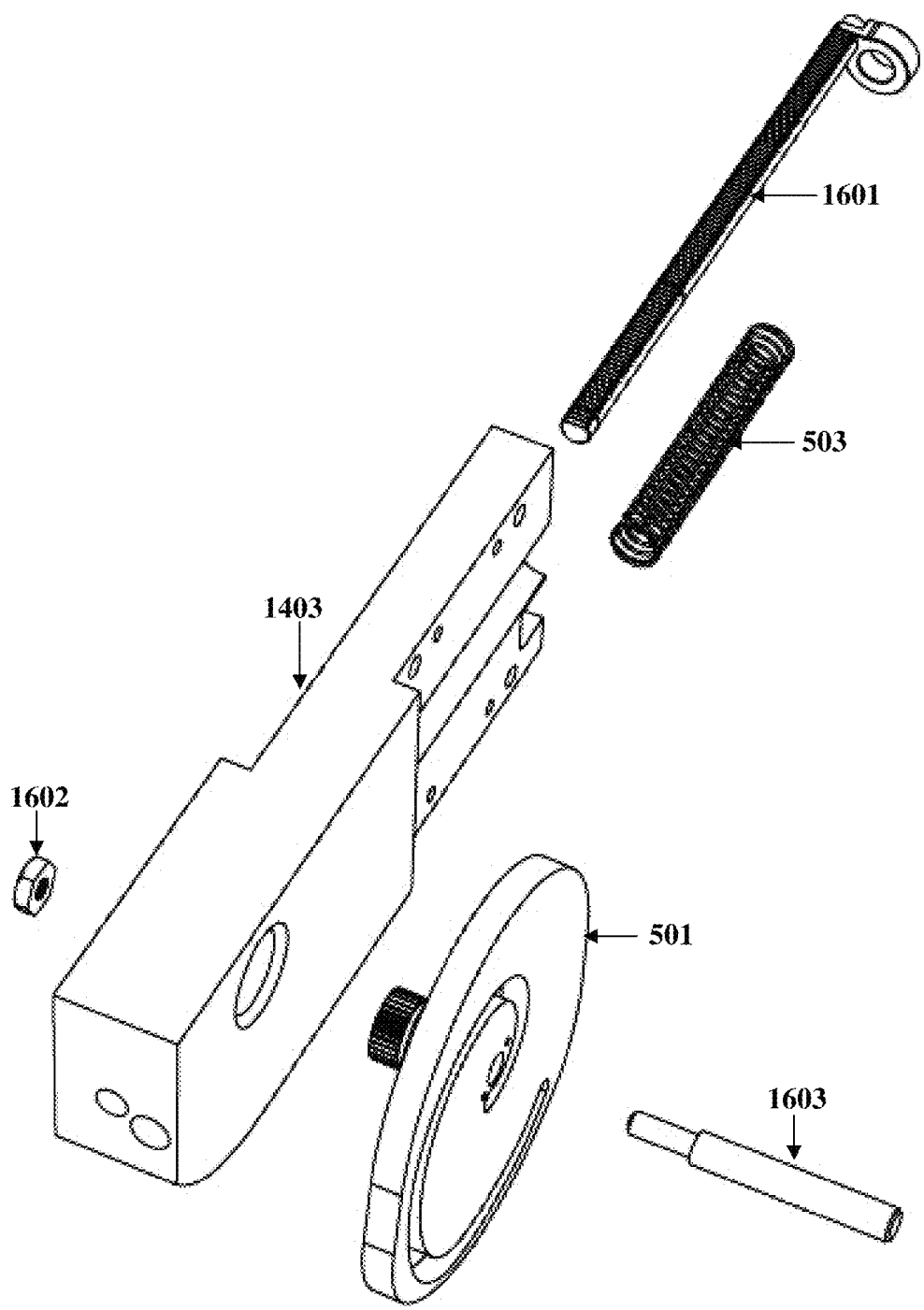
FIG. 16 exemplarily illustrates an exploded view of the tail block of the chassis subassembly.

FIG. 16 exemplarily illustrates an exploded view of the tail block 1403 of the chassis subassembly 1201. The tail block 1403 comprises the shifter plate 501, the return spring 503, and a shifter rack subassembly 1601. The shifter plate 501 rotates upon a second axle 1603. The second axle 1603 may be secured to the tail block 1403 with an axle nut 1602. The shifter rack subassembly 1601 translates the length of the shifter rod 504 into rotation of the shifter plate 501.

Figure 17:
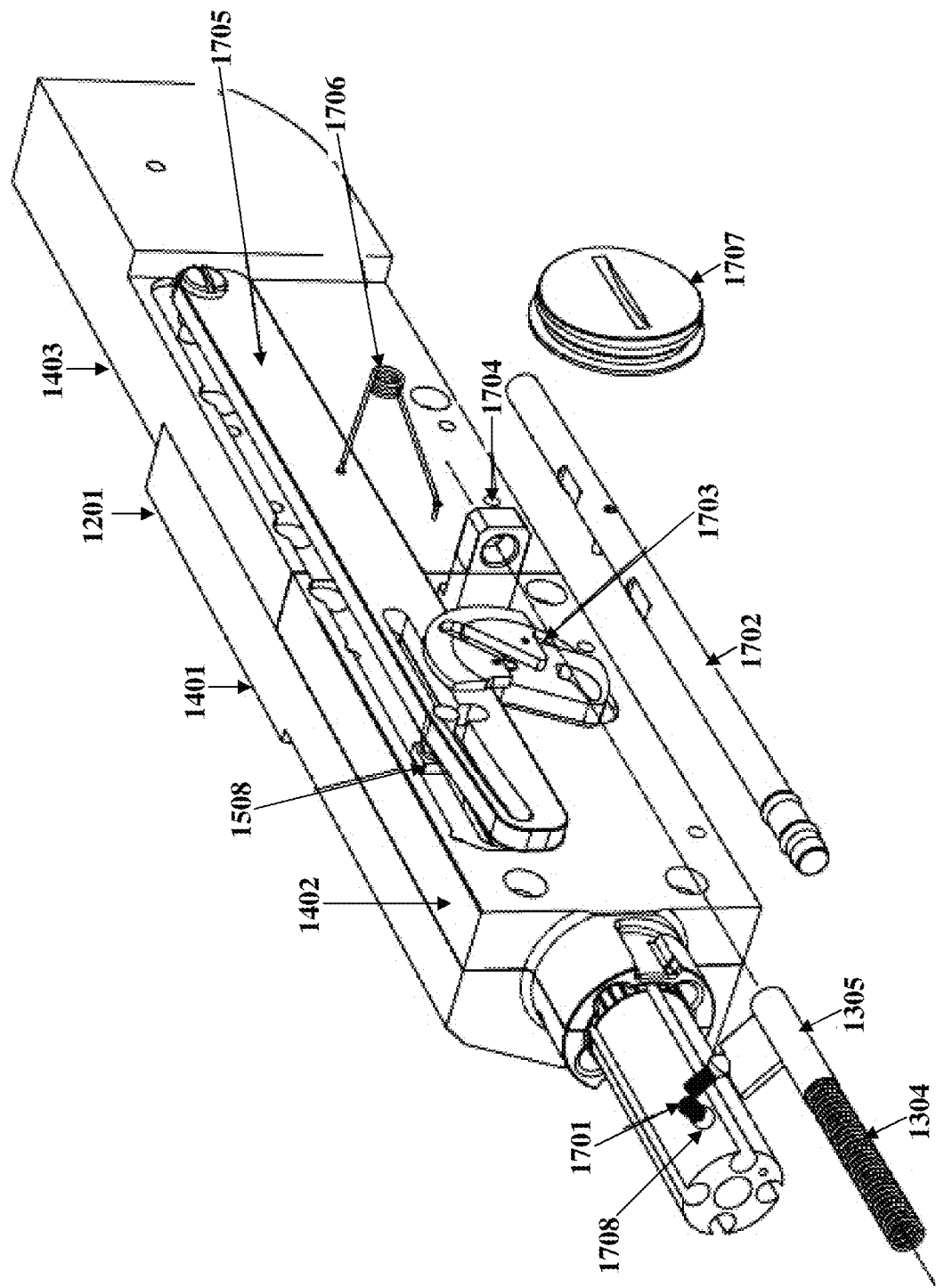
FIG. 17 exemplarily illustrates an isometric view of the chassis subassembly with the main block, the side block, and the tail block assembled together highlighting the neutral lock-out system.

FIG. 17 exemplarily illustrates an isometric view of the chassis subassembly 1201 with the main block 1401, the side block 1402, and the tail block 1403 assembled together highlighting the neutral lock-out system. The chassis subassembly 1201 may further incorporate a neutral lock-out system comprising one or more NLO balls 1708, one or more NLO springs 1701, an NLO drive rod subassembly 1702, an NLO cam subassembly 1703, an NLO drive rod steady 1704, an NLO gate 1705, an NLO gate spring 1706, and an NLO knob subassembly 1707.

The NLO drive rod subassembly 1702 pins the housings of the shaft assembly 102*a* and the operator control section assembly 101 together and to restrict relative rotation. This NLO drive rod subassembly 1702 is withdrawn to release the quarter-turn bayonet for disconnecting the shaft assembly 102*a* and the operator control section assembly 101. The NLO cam subassembly 1703 controls the position of the NLO drive rod subassembly 1702. The NLO gate 1705 reads the position of the NLO post 1504 attached to the adaptable drive transmission system 500 and restricts rotation of the NLO cam subassembly 1703. The NLO gate spring 1706 provides tension to the NLO gate 1705 to maintain contact with the NLO post 1504. The NLO knob subassembly 1707 enables the operator to rotate the NLO cam subassembly 1703. The NLO balls 1708 and the NLO springs 1701 together form a detent for rotation of the post subassembly 1202.

Figure 20:
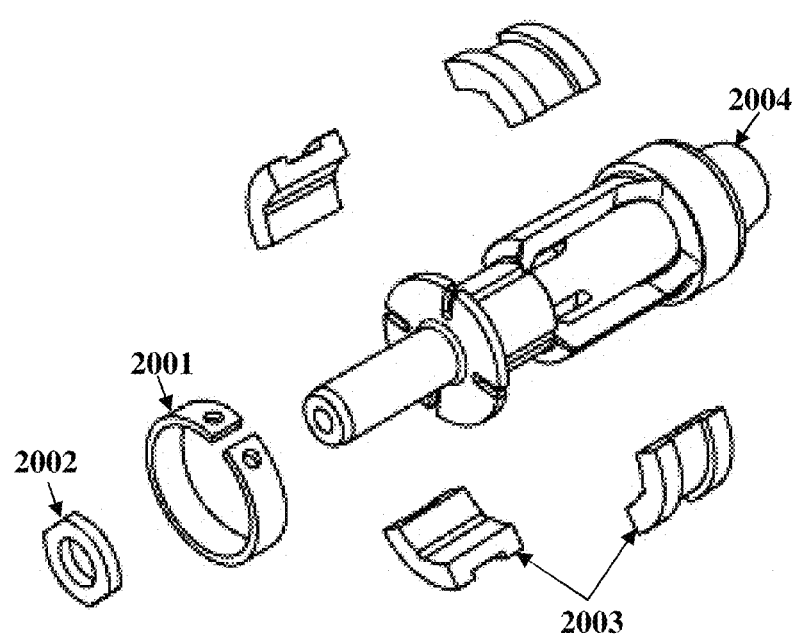
FIG. 20 exemplarily illustrates an exploded view of the sheath anchor subassembly.

FIG. 20 exemplarily illustrates an exploded view of the sheath anchor subassembly 1905. The sheath anchor subassembly 1905 comprises a clamp ring 2001, a jam nut 2002, multiple sheath anchor collets 2003, and a sheath anchor 2004. The clamp ring 2001 secures the sheath anchor collets 2003. The jam nut 2002 locks the threaded end of the sheath anchor 2004 when screwed into the post subassembly 1202. The sheath anchor collets 2003 are individual pieces for holding the proximal ends of the cable sheaths 1105 against the anchor.

Figure 21:
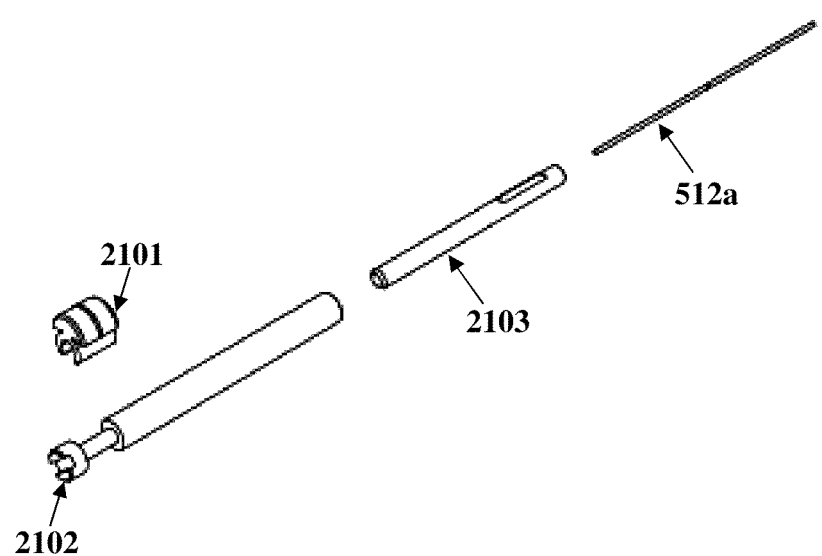
FIG. 21 exemplarily illustrates an exploded view of one of the control rod subassemblies.

FIG. 21 exemplarily illustrates an exploded view of one of the control rod subassemblies 1803. Each of the control rod subassemblies 1803 comprises a control rod tab 2101, a female control line anchor 2102, a male control line anchor 2103, and a principal cable wire 512*a* or 512*b* or a proxy cable wire 513*a* or 513*b*. For purposes of illustration, FIG. 21 exemplarily illustrates a principal cable wire 512*a*. The male control line anchor 2103 enables attachment of the control rod subassembly to a free end of the cable wires. The female control line anchor 2102 forms the telescoping screw 1805 in conjunction with the male control line anchor 2103 that enables fine-tune adjustment of the working length of the cable wires. The principal cable wire 512*a* or 512*b* or the proxy cable wire 513*a* or 513*b* provides interfacing features for connecting the control rod subassembly to the adaptable drive transmission system 500.

The control rod tab 2101 allows the shaft assembly 102*a* to be separated from the operator control section assembly 101. Multiple control rod tabs may be provided in different channels of the post 1504. The control rod tabs may be arrayed at 90 degrees from each other. When the portable endoscope 100 is assembled, two of the control rod tabs, for example, the control rod tabs corresponding to the principal cable wires 512*a* and 512*b*, may be engaged with the cable wire anchor boxes 508 at the ends of the top driven rack subassembly 510*a* and the bottom driven rack subassembly 510*b*, which are connected to the adaptable drive transmission 500. Two other control rod tabs, for example, the control rod tabs corresponding to the proxy cable wires 513*a* and 513*b*, may be locked in fixed pockets and not allowed to move. In the neutral position the control rod tabs are aligned and the post subassembly 1202 may be rotated so that the control rod tabs may be disengaged from the cable wire anchor boxes 508 of the top driven rack subassembly 510*a* and the bottom driven rack subassembly 510*b*, and the fixed pockets. When the post subassembly 1202 is rotated by 90 degrees clockwise, the control rod tabs corresponding to the principal cable wires 512*a* and 512*b* exchange places with the control rod tabs corresponding to the proxy cable wires 513a and 513b. When the post subassembly 1202 is rotated by 45 degrees counter clockwise, the control rod tabs are simultaneously disengaged but aligned with respective exit paths provided within the chassis subassembly 1201 for allowing the post subassembly 1202 to be withdrawn axially from the operator control section assembly 101.

To change the shaft assembly 102a, the operator first sets the portable endoscope 100 to the neutral position by moving the steering lever 103 to a neutral position. The operator then sets the safety switch 108 to the third operational position, causing the adaptable drive transmission 500 to be locked in a neutral position. The quick disconnect subassembly is unlocked from the operator control section assembly 101. The operator then rotates the quick disconnect subassembly by 45 degrees in a counter-clockwise direction relative to the operator control section assembly 101, causing the control rod tabs to be disengaged from the cable wire anchor boxes 508. The operator may then withdraw the post subassembly 1202 from the operator control section assembly 101. The operator may select an alternative shaft assembly 102a and reverse the procedure described above to reassemble the portable endoscope 100 with the alternative shaft assembly 102a.

The portable endoscope 100 disclosed herein may be included in a portable endoscope kit with component parts capable of being assembled in the field. The portable endoscope kit comprises an operator control section assembly 101 and multiple shaft assemblies 102a, 102b, and 102c. A first shaft assembly 102a, 102b, or 102c from the shaft assemblies 102a, 102b, and 102c is configured for an endoscopic purpose different from a second shaft assembly 102a, 102b, or 102c from the shaft assemblies 102a, 102b, and 102c. Each of the shaft assemblies 102a, 102b, and 102c comprises an elongated body with a flexible distal end 105a and a proximal end. Each of the flexible distal ends and each of the elongated bodies are configured for insertion into an internal cavity of a body of an organism, or a similarly otherwise inaccessible internal space. The proximal end of each of the shaft assemblies 102a, 102b, and 102c is configured for selectable engagement between the proximal end and the operator control section assembly 101. The operator control section assembly 101 is configured to engage the proximal end of any one of the shaft assemblies 102a, 102b, and 102c. The flexible distal end 105a of each of the shaft assemblies 102a, 102b, and 102c is locally bendable. Each of the shaft assemblies 102a, 102b, and 102c and the operator control section assembly 101 are configured so that the operator control section assembly 101 selectably controls the local bending of the flexible distal end 105a of the shaft assembly 102a, 102b, or 102c when the shaft assembly 102a, 102b, or 102c is in the selectable engagement with the operator control section assembly 101.

The portable endoscope kit further comprises an internal cable wire control system 514 integrated with the operator control section assembly 101. The internal cable wire control system 514 utilizes an adaptable drive transmission system 500 for controlling orientation and angular position of the flexible distal end 105a of the shaft assembly 102a using principal cable wires 512a and 512b and proxy cable wires 513a and 513b. The adaptable drive transmission system 500 comprises an angulation and deflection gear system 502 comprising gears and gear track subassemblies for matching operator input to steering output of the portable endoscope 100. The neutral lock-out system and the quick disconnect subassembly facilitate engagement and disengagement of the principal cable wires 512a and 512b and the proxy cable wires 513a and 513b.

The portable endoscope kit may further comprise an optical imaging system 112 and an illumination system 1101. The portable endoscope kit may further comprise an external light source in communication with the illumination system 1101 and the optical imaging system 112. The external light source provides light to the illumination system 1101 and the optical imaging system 112. The portable endoscope kit may further comprise a cable wire switch 110 integrated with the shaft assemblies 102a, 102b, and 102c to engage the principal cable wires 512a and 512b or the proxy cable wires 513a and 513b.

The portable endoscope kit may further comprise an image capturing system integrated with detachable operator control section assembly 101, wherein the image capturing system comprises image sensors for capturing and transmitting visual images. The image sensors may, for example, comprise a charge coupled display, a complementary metal oxide semiconductor image sensor, or a contact image sensor. The portable endoscope kit may further comprise a working channel turret 104 integrated with the shaft assembly 102a for aiding medical lavage, aspiration, biopsy, or manipulation procedures. The portable endoscope kit may further comprise a suction and irrigation control system for controlling flow of fluids during a medical lavage or aspiration procedure. The suction and irrigation control system may be detachably attached to the operator control section assembly 101.

Figure 22:
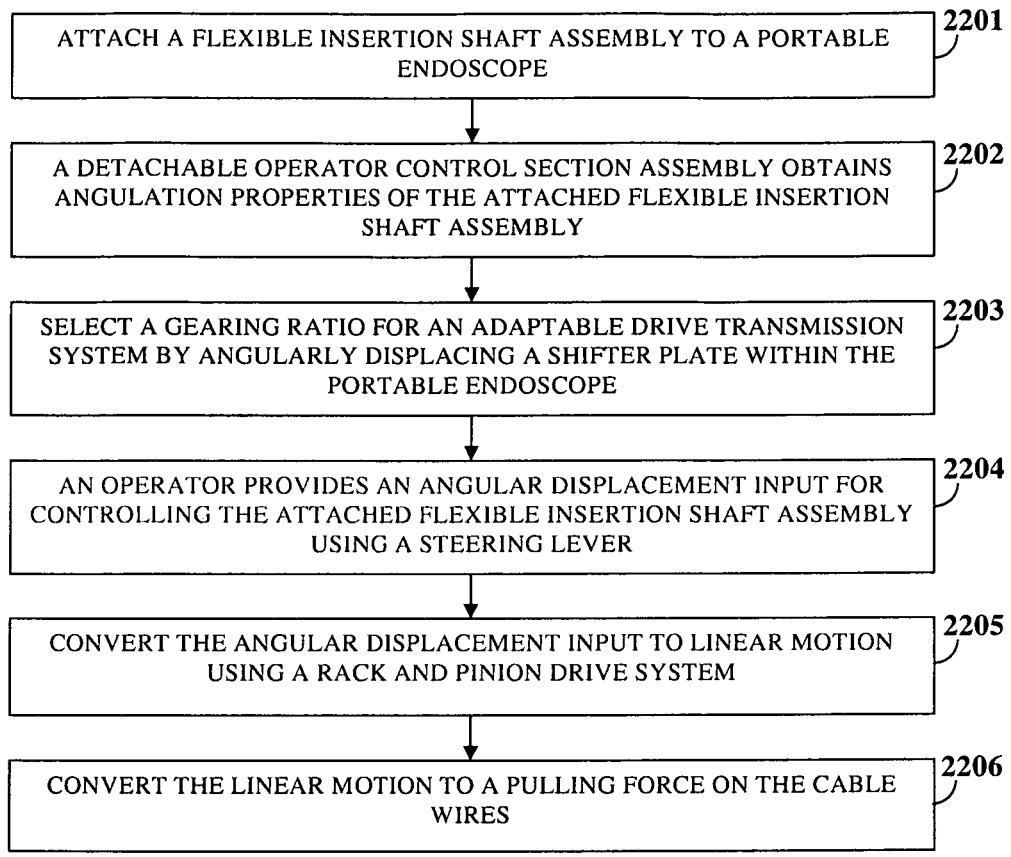
FIG. 22 illustrates a method of adaptably driving a flexible insertion shaft assembly of a portable endoscope using an adaptable drive transmission system.

FIG. 22 illustrates a method of adaptably driving a shaft assembly 102a of a portable endoscope 100 using an adaptable drive transmission system 500 of the portable endoscope 100. The shaft assembly 102a is attached 2201 to the portable endoscope 100. The attached shaft assembly 102a is connected to principal cable wires 512a and 512b and proxy cable wires 513a and 513b. The detachable operator control section assembly 101 obtains 2202 angulation properties of the attached shaft assembly 102a. As used herein, the angulation properties of a shaft assembly 102a refers to properties of the shaft assembly 102a relating to the deflection of the flexible distal end 105a of the shaft assembly 102a. For example, the angulation properties may be maximum angle of deflection, optimum range of deflection, etc. of the flexible distal end 105a of the shaft assembly 102a.

A gearing ratio for the adaptable drive transmission system 500 is selected 2203 by angularly displacing a shifter plate 501 within the portable endoscope 100. The amount of angular displacement is based on the angulation properties and determines the selected gearing ratio. An operator provides 2204 an angular displacement input for controlling the attached shaft assembly 102a using a steering lever 103 of the portable endoscope 100. An angulation and deflection gear system 502 connected to the steering lever 103 converts 2205 the angular displacement input to linear motion using a rack and pinion drive system 507. The amount of the linear motion obtained relative to the angular displacement input is determined by the selected gearing ratio. For example, if a high gearing ratio is selected, a small angular displacement of the steering lever 103 may be translated to a large amount of linear motion. If a low gearing ratio is selected, the same amount of angular displacement of the steering lever 103 may be translated to a small amount of linear motion. The linear motion is converted 2206 to a pulling force on the principal cable wires 512a and 512b and the proxy cable wires 513a and 513b. The amount of the pulling force is based on the amount of the linear motion. The attached shaft assembly 102a is thus adaptably driven by the pulling force.

Figure 23:
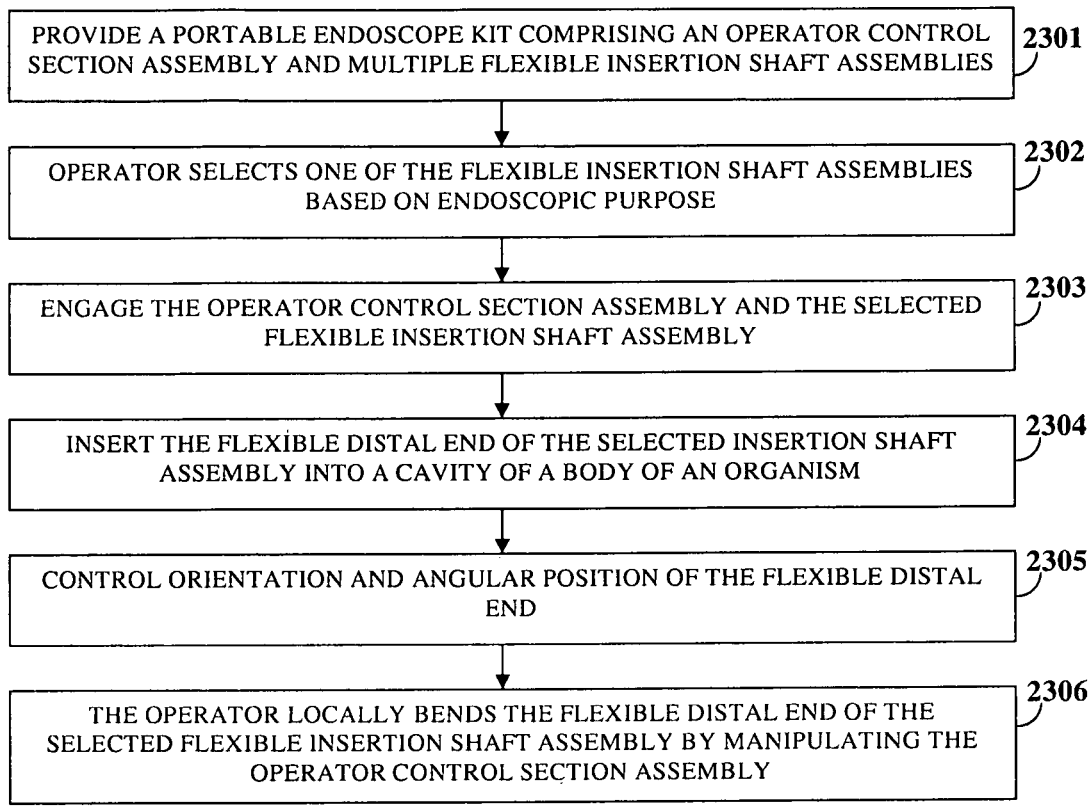
FIG. 23 illustrates a method of performing an endoscopic examination using a portable endoscope kit.

FIG. 23 illustrates a method of performing an endoscopic examination using a portable endoscope kit. The portable endoscope kit capable of being assembled by an operator is provided 2301. The portable endoscope kit comprises an operator control section assembly 101 and multiple shaft assemblies 102a, 102b, and 102c. A first shaft assembly 102a, 102b, or 102c from the shaft assemblies 102a, 102b, and 102c is configured for an endoscopic purpose different from a second shaft assembly 102a, 102b, or 102c from the shaft assemblies 102a, 102b, and 102c. Each of the shaft assemblies 102a, 102b, and 102c comprises an elongated body with a locally bendable flexible distal end 105a. The operator selects 2302 one of the shaft assemblies 102a, 102b, and 102c based on the endoscopic purpose.

The operator engages 2303 the operator control section assembly 101 and the selected shaft assembly 102a. The operator control section assembly 101 controls bending of the flexible distal end 105a of the selected shaft assembly 102a. The flexible distal end 105a of the selected shaft assembly 102a is inserted 2304 into a cavity of a body of an organism, or a similarly otherwise inaccessible internal space. The operator controls 2305 orientation and angular position of the flexible distal end 105a using the principal cable wires 512a and 512b or the proxy cable wires 513a and 513b. The principal cable wires 512a and 512b and the proxy cable wires 513a and 513b are controlled using an adaptable drive transmission system 500. The operator locally bends 2306 the flexible distal end 105a of the elongated body of the selected shaft assembly 102a by manipulating the operator control section assembly 101.

The foregoing examples have been provided merely for the purpose of explanation and are in no way to be construed as limiting of the present invention. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A method of adaptably driving a flexible insertion shaft assembly of a portable endoscope using an adaptable drive transmission system of said portable endoscope, comprising the steps of:
    attaching said flexible insertion shaft assembly to the portable endoscope, wherein said attached flexible insertion shaft assembly is connected to a plurality of cable wires, and wherein said cable wires comprise principal cable wires and proxy cable wires:
    obtaining angulation properties of the attached flexible insertion shaft assembly by a detachable operator control section assembly;
    selecting a gearing ratio for said adaptable drive transmission system by angularly displacing a shifter plate within the portable endoscope, wherein amount of said angular displacement is based on said angulation properties and determines said selected gearing ratio;
    providing an angular displacement input for controlling the attached flexible insertion shaft assembly by an operator using a steering lever, wherein said steering lever manipulates movement of one of the principal cable wires and the proxy cable wires via the adaptable drive transmission system based on engagement of one of the principal cable wires and the proxy cable wires by a cable wire switch integrated with the attached flexible insertion shaft assembly;
    engaging one of the principal cable wires and the proxy cable wires with said adaptable drive transmission system by said cable wire switch, said cable wire switch being rotatable to disengage and dissociate the principle cable wire from the adaptable drive transmission system, wherein a neutral lock-out system and a quick disconnect subassembly facilitates engagement and disengagement of the principal cable wires and the proxy cable wires such that said adaptable drive transmission system may be engaged with said proxy cable wires using said cable wire switch;
    converting said angular displacement input to linear motion using a rack and pinion drive system by an angulation and deflection gear system connected to said steering lever, wherein amount of said linear motion obtained relative to the angular displacement input is determined by the selected gearing ratio, wherein said angulation and deflection gear system comprises gears and gear track subassemblies for matching operator input to scope steering output; and
    converting the linear motion to a pulling force on said cable wires, wherein amount of said pulling force is based on said amount of the linear motion;
    whereby the attached flexible insertion shaft assembly is adaptably driven by the pulling force.

2. The method of claim 1, wherein creating a seal between housings of the shaft assembly and operator control section assembly to maintain sterility of internal workings by an "O" shaped ring.

3. The method of claim 1, wherein utilizing the proxy cable wires for controlling a flexible distal end of the attached flexible insertion shaft assembly in an event of failure of the principal cable wires during medical procedures in progress by an internal cable wire control system, wherein said cable wire switch disengages the principal cable wires from the adaptable drive transmission system and engages the proxy cable wires with the adaptable drive transmission system.

* * * * *